United States Patent
Augeri et al.

(10) Patent No.: US 6,288,261 B1
(45) Date of Patent: Sep. 11, 2001

(54) INHIBITORS OF MATRIX METALLOPROTEINASES

(75) Inventors: David J. Augeri, Princeton; David A. Betebenner, Lawrenceville, both of NJ (US); Richard Craig, Racine, WI (US); Steven K. Davidsen, Libertyville; Stephen W. Fesik, Gurnee, both of IL (US); Jamie R. Giesler-Stacey, Racine, WI (US); Yan Guo, Gurnee, IL (US); Philip J. Hajduk, Mundelein, IL (US); Michael R. Michaelides, Libertyville, IL (US); David G. Nettesheim, Lake Forest, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/465,232

(22) Filed: Dec. 14, 1999

Related U.S. Application Data

(60) Provisional application No. 60/112,940, filed on Dec. 18, 1998.

(51) Int. Cl.[7] .................................................. C07C 255/00
(52) U.S. Cl. ...................... 558/404; 514/239.2; 514/386; 514/568; 514/618; 514/709; 562/622
(58) Field of Search ........................ 558/404; 514/239.2, 514/386, 568, 618, 709; 562/622

(56) References Cited

U.S. PATENT DOCUMENTS

| | | |
|---|---|---|
| 4,859,706 | 8/1989 | Buerstinghaus et al. ............. 514/624 |
| 4,981,865 | 1/1991 | Belliotti et al. ....................... 514/480 |
| 4,996,358 | 2/1991 | Handa et al. ......................... 562/621 |
| 5,300,501 | 4/1994 | Porter et al. ........................ 514/238.2 |
| 5,442,110 | 8/1995 | Isomura et al. ....................... 562/621 |
| 5,605,923 | 2/1997 | Christensen, IV et al. ........... 514/417 |
| 6,013,649 * | 1/2000 | Freskos et al. ..................... 514/237.8 |
| 6,037,472 * | 3/2000 | Castelhano et al. ............... 546/269.7 |
| 6,153,757 * | 11/2000 | Zook et al. ........................... 546/301 |
| 6,166,005 * | 12/2000 | De et al. .......................... 514/211.01 |
| 6,194,451 * | 2/2001 | Alpegiani et al. ................... 514/459 |

FOREIGN PATENT DOCUMENTS

| | | |
|---|---|---|
| 0196184 | 10/1986 | (EP) . |
| 0489577 | 6/1992 | (EP) . |
| 0498665 | 8/1992 | (EP) . |
| 0575844 | 12/1993 | (EP) . |
| 9102716 | 3/1991 | (WO) . |
| 9213831 | 8/1992 | (WO) . |
| 9324449 | 12/1993 | (WO) . |
| 9402446 | 2/1994 | (WO) . |
| 9402447 | 2/1994 | (WO) . |
| 9402448 | 2/1994 | (WO) . |
| 9410990 | 5/1994 | (WO) . |
| 9421612 | 9/1994 | (WO) . |
| 9422309 | 10/1994 | (WO) . |
| 9424140 | 10/1994 | (WO) . |
| 9425435 | 11/1994 | (WO) . |
| 9504735 | 2/1995 | (WO) . |
| 9506031 | 3/1995 | (WO) . |
| 9519956 | 7/1995 | (WO) . |
| 9519961 | 7/1995 | (WO) . |
| 9522966 | 8/1995 | (WO) . |
| 9523790 | 9/1995 | (WO) . |
| 9529892 | 11/1995 | (WO) . |
| 9532944 | 12/1995 | (WO) . |
| 9533731 | 12/1995 | (WO) . |
| 9615096 | 5/1996 | (WO) . |
| 9616027 | 5/1996 | (WO) . |
| 9616931 | 6/1996 | (WO) . |
| 9633161 | 10/1996 | (WO) . |
| 9718188 | 5/1997 | (WO) . |
| 9718207 | 5/1997 | (WO) . |
| 9838179 | 9/1998 | (WO) . |
| WO 2000037433 * | 6/2000 | (WO) . |

\* cited by examiner

*Primary Examiner*—Ralph Gitomer
*Assistant Examiner*—D Khare
(74) *Attorney, Agent, or Firm*—Gregory W. Steele; B. Gregory Donner

(57) ABSTRACT

Compounds having the formula

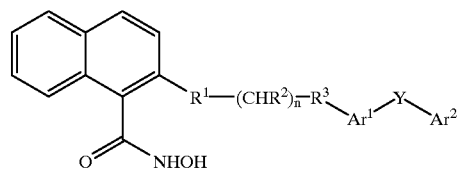

and pharmaceutically acceptable salts and prodrugs thereof are matrix metalloproteinase inhibitors. Also disclosed are matrix metalloproteinase-inhibiting compositions and methods of inhibiting matrix metalloproteinase in a mammal.

14 Claims, No Drawings

INHIBITORS OF MATRIX METALLOPROTEINASES

This application claims the benefit of the provisional U.S. application Ser. No. 60/112,940, filed on Dec. 18, 1998.

TECHNICAL FIELD

This invention relates to compounds having activity to inhibit matrix metalloproteinases, to pharmaceutical compositions comprising these compounds, and to a medical method of treatment using the compounds.

BACKGROUND OF THE INVENTION

The matrix metalloproteinases (MMP's) are a class of extracellular enzymes including collagenase, stromelysin, and gelatinase which are believed to be involved in the tissue destruction which accompanies a large number of disease states varying from arthritis to cancer.

Typical connective tissue cells are embedded within an extracellular matrix of high molecular weight proteins and glycoproteins. In healthy tissue, there is a continual and delicately-balanced series of processes which include cell division, matrix synthesis and matrix degradation. In certain pathological conditions, an imbalance of these three processes can lead to improper tissue restructuring. In arthritis, for example, joint mobility can be lost when there is improper remodeling of load-bearing joint cartilage. With cancer, lack of coordination of cell division and the two processes of matrix synthesis and degradation may lead to conversion of transformed cells into invasive phenotypes in which increased matrix turnover permits tumor cells to penetrate basement membranes surrounding capillaries which, in turn, can lead to subsequent metastasis.

Thus there has been heightened interest in discovering therapeutic agents which bind to and inhibit MMP's. The discovery of new therapeutic agents possessing this activity will lead to new drugs having a novel mechanism of action for combating disease states involving tissue degenerative processes including, for example, rheumatoid arthritis, osteoarthritis, osteopenias such as osteoporosis, periodontitis, gingivitis, corneal, epidermal or gastric ulceration, and tumor growth and metastasis or invasion.

SUMMARY OF THE INVENTION

In its principle embodiment, the present invention provides a matrix metalloproteinase inhibiting compound of formula I:

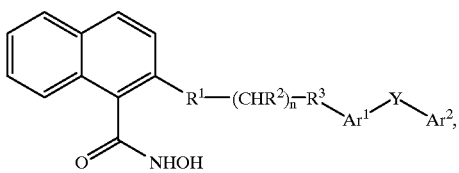

I or a pharmaceutically acceptable salt or produrug thereof, wherein $R^1$ is selected from the group consisting of (a) a covalent bond, (b) —O—, and (c) —S(O)$_q$—wherein q is 0, 1, or 2;

$R^2$ is hydrogen or alkyl;

$R^3$ is selected from the group consisting of (a) —HNSO$_2$—, (b) —O—, (c) S(O)$_q$—, (d) —C(=O)—, and (e) —C(=NOH)—; and n is 1, 2, or 3;

$Ar^1$ is phenyl substituted with 0, 1, or 2 substituents independently selected from the group consisting of (a) alkyl, (b) perfluoroalkyl, (c) halo, (d) haloalkyl, (e) alkoxy, (f) hydroxy, (g) hydroxyalkyl, (h) alkoxyalkyl, and (i) nitro;

Y is selected from the group consisting of (a) a covalent bond, (b) —O—, (c) alkylene, (d) piperidineneyl, (e) alkenylene, (f) alkynylene, (g) —S(O)$_q$—, (h) —NHC(=O)—, and (i) —C(=O)—; and $Ar^2$ is selected from the group consisting of (a) phenyl, (b) pyridyl, (c) pyrazinyl, (d) pyridazinyl, (e) furyl, (f) thienyl, (g) isoxazolyl, (h) oxazolyl, (i) thiazolyl, and (j) isothiazolyl wherein the groups defining $Ar^2$ are substituted with 0, 1, 2, or 3 substituents independently selected from the group consisting of (1) alkyl, (2) alkoxy, (3) alkoxyalkoxy, (4) alkyloxycarbonylalkyl, (5) alkoxyalkyl, (6) cyano, (7) cyanoalkyl, (8) halo, (9) haloalkyl, (10) hydroxy, (11) hydroxyalkyl, (12) thioalkoxy, (13) thioalkoxyalkyl, (14) phenylalkoxy, (15) phenoxy, (16) —N($R^2$)SO$_2$$R^{2'}$ wherein $R^2$ is defined previously and $R^{2'}$ is hydrogen or alkyl, (17) —SO$_2$N($R^2$)($R^{2'}$) wherein $R^2$ and $R^{2'}$ are defined previously, (18) phenoxyalkyl, (19) (heterocycle)oxy, (20) (heterocycle)oxyalkyl, (21) perfluoroalkyl, (22) perfluoroalkoxy, (23) sulfinylalkyl, (24) sulfonylalkyl, (25)

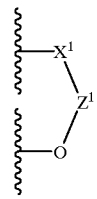

wherein $X^1$ is selected from the group consisting of —CH$_2$—, —CH$_2$O— and —O—, and $Z^1$ is —C(=O)— or —(C($R^2$)$_2$)$_v$— wherein $R^2$ is defined previously and v is 1–3, and (26) -alkyl-NR$^x$R$^y$ wherein R$^x$ and R$^y$ are independently selected from the group consisting of (i) alkyl, (ii) phenyl substituted with 0, 1, or 2 substituents selected from the group consisting of halo and alkoxy, and (iii) phenylalkyl wherein the phenyl group is substituted with 0, 1, or 2 substituents selected from the group consisting of halo and alkoxy.

In another embodiment, the present invention provides a compound of formula I wherein $R^1$ is a covalent bond and $R^3$ is —O—.

In another embodiment, the present invention provides a compound of formula I wherein $R^1$ is —O— or a covalent bond and $R^3$ is —C(=O)— or —C(=NOH)—.

In another embodiment, the present invention provides a compound of formula I wherein $R^1$ is —O— and $R^3$ is —S(O)$_q$— wherein q is defined previously.

In another embodiment, the present invention provides a compound of formula I wherein $R^1$ is a covalent bond and $R^3$ is —S(O)$_q$— wherein q is defined previously.

In another embodiment, the present invention provides a compound of formula I wherein $R^1$ is a covalent bond and $R^3$ is —NHSO$_2$—.

In another embodiment, the present invention provides a compound of formula I wherein $R^1$ and $R^3$ are —O—.

In another embodiment, the present invention provides pharmaceutical compositions which comprise a therapeutically effective amount of compound of formula I in combination with a pharmaceutically acceptable carrier.

In another embodiment, the present invention provides a method of inhibiting matrix metalloproteinases in a host mammal in need of such treatment comprising administering a therapeutically effective amount of a compound of formula I.

DETAILED DESCRIPTION OF THE INVENTION

Definition of Terms

As used throughout this specification and the appended claims, the following terms have the meanings specified.

The term "alkanoyl," as used herein, refers to an alkyl group, as defined below, attached to the parent molecular moiety through a —C(=O)— group. Examples of alkanoyl groups include acetyl, propionyl, butanoyl, and the like.

The term "alkenyl," as used herein, refers to a monovalent straight or branched chain of two to six carbon atoms containing at least one carbon-carbon double bond derived from an alkene by the removal of one hydrogen atom. Examples of alkenyl groups include ethenyl, 1-propenyl, 2-propenyl, 2-methyl-1-propenyl, 1-butenyl, 2-butenyl, and the like.

The term "alkenylene," as used herein, refers to a straight or branched chain hydrocarbon of two to ten carbon atoms containing at least one carbon-carbon double bond derived from an alkene by the removal of two hydrogen atoms. Examples of alkenylene groups include —CH=CH—, —CH$_2$CH=CH—, —C(CH$_3$)=CH—, —CH$_2$CH=CHCH$_2$—, and the like.

The term "alkoxy," as used herein, refers to an alkyl group, as defined below, attached to the parent molecular moiety through an oxygen atom. Examples of alkoxy groups include methoxy, ethoxy, propoxy, butoxy, and the like.

The term "alkoxyalkoxy," as used herein, refers to an alkoxy group, as defined above, attached to an alkoxy group, as defined above. Examples of alkoxyalkoxy groups include ethoxyethoxy, ethoxymethoxy, methoxymethoxy, and the like.

The term "alkoxyalkyl," as used herein, refers to an alkoxy group, as defined above, attached to the parent molecular moiety through an alkyl group, as defined below. Examples of alkoxyalkyl groups include —CH$_2$OCH$_3$, —CH$_2$CH$_2$OCH$_3$, —CH$_2$CH$_2$OCH$_2$CH$_3$, and the like.

The term "alkoxycarbonyl," as used herein, refers to an alkoxy group, as defined above, which is attached to the parent molecular group through a —C(=O)— group. Examples of alkoxycarbonyl include methoxycarbonyl, ethoxycarbonyl, tert- butoxycarbonyl, and the like.

The term "alkoxycarbonylalkyl," as used herein, refers to an alkoxycarbonyl group, as defined above, which is attached to the parent molecular group through an alkyl group as defined below. Examples of alkoxycarbonylalkyl include methoxycarbonylmethyl, ethoxycarbonylpropyl, tert-butoxycarbonylbutyl, and the like.

The term "alkyl," as used herein, refers to a monovalent group derived from a straight or branched chain saturated hydrocarbon of one to ten carbon atoms by the removal of a single hydrogen atom. Examples of alkyl groups are methyl, ethyl, n-propyl, iso-propyl, n-butyl, sec-butyl, iso-butyl and tert-butyl, and the like.

The term "alkylene," as used herein, refers to a divalent group derived from a straight or branched chain saturated hydrocarbon of one to ten carbon atoms by the removal of two hydrogen atoms. Examples of alkylene groups include —CH$_2$—, —CH$_2$CH$_2$—, —CH(CH$_3$)CH$_2$—, and the like.

The term "alkynylene," as used herein, refers to a divalent group derived from a straight or branched chain hydrocarbon of two to ten carbon atoms derived by the removal of two hydrogen atoms from a group containing at least one carbon-carbon triple bond.

The term "aryl," as used herein, refers to a mono- or bicyclic carbocyclic ring system having one or two aromatic rings. The aryl group can also be fused to a cyclohexane, cyclohexene, cylopentane, or cylopentene ring. Aryl groups of the invention can be optionally substituted. The term "benzyloxy," as used herein, refers to —O—(CH$_2$)-phenyl.

The term "cyano," as used herein, refers to —CN.

The term "cyanoalkyl," as used herein, refers to an alkyl group, as defined above, substituted by at least one cyano group. Examples of cyanoalkyl groups include cyanomethyl, cyanoethyl, cyanopropyl, and the like.

The term "cycloalkenyl," as used herein, refers to a monovalent group containing at least one carbon-carbon double bond derived from a cyclic or bicyclic hydrocarbon of three to twelve carbons by the removal of one hydrogen atom. Examples of cycloalkenyl groups include cyclobutene, cyclopentene, cyclohexene, bicyclo[2.2.1]heptene, and the like.

The term "cycloalkyl," as used herein, refers to a monovalent group derived from a saturated cyclic hydrocarbon group of three to ten carbons by the removal of one hydrogen atom. Examples of cycloalkyl groups include cyclopropyl, cyclobutyl, cyclopentyl, cyclohexyl, cycloheptyl, bicyclo[2.2.1]heptyl, and the like.

The term "(cycloalkyl)alkyl," as used herein, refer to a cycloalkyl group, as defined above, attached to the parent molecular moiety through an alkylene group, as defined above.

The term "(cycloalkenyl)alkyl," as used herein, refer to a cycloalkenylene group, as defined above, attached to the parent molecular moiety through an alkylene group, as defined above.

The term "halo" or "halogen," as used herein, refers to —F, —Cl, —Br, and —I.

The term "haloalkyl," as used herein, refers to an alkyl group, as defined above, to which is attached at least one halogen atom. Examples of haloalkyl groups include chloromethyl, bromoethyl, trifluoromethyl, and the like.

The term "heterocycle," as used herein, refers to a monovalent group derived from a five, six, or seven membered ring containing one, two, or three heteroatoms independently selected from the group consisting of nitrogen, oxygen and sulfur by the removal of one hydrogen atom. The five membered ring has zero to two double bonds and the six and seven membered rings have zero to three double bonds. Hererocycles include indolyl, quinolyl, isoquinolyl, tetrahydroquinolyl, benzofuryl, benzothienyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiomorpholino sulfone, thiazolyl, thiazolidinyl, isothiazolyl, isothiazolidinyl, indolyl, quinolinyl, isoquinolinyl, benzimidazolyl, benzothiazolyl, benzoxazolyl, fuiryl, thienyl, thiazolidinyl, isothiazolyl, triazolyl, tetrazolyl, oxadiazolyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl, succinimidyl, maleimidyl, lutarimidyl, phthalimidyl, naphthalimidyl, and the like. Heterocycles also include

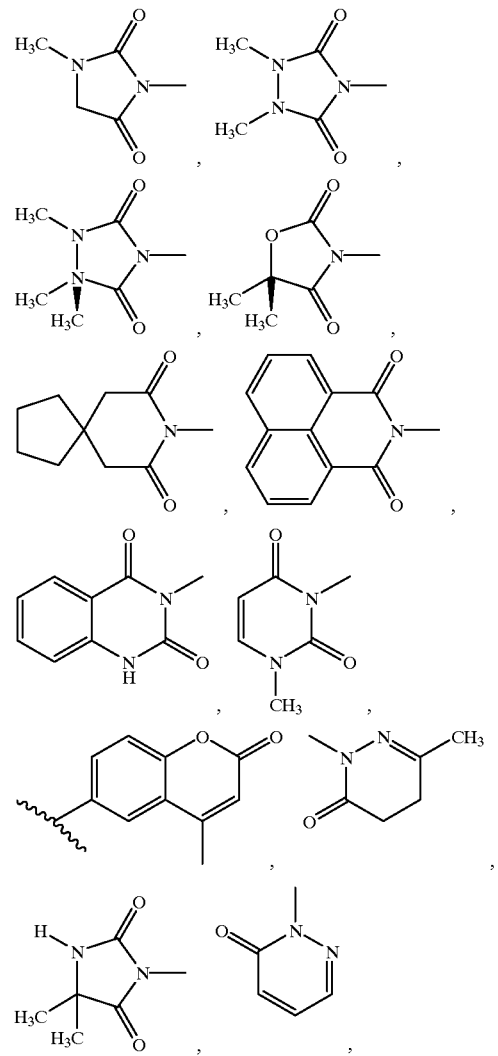

and the like. Heterocycle groups of the invention can be optionally substituted.

The term "(heterocycle)oxy," as used herein, represents a heterocycle group, as defined above, attached to the parent molecular moiety through an oxygen atom.

The term "(heterocycle)oxyalkyl," as used herein, represents a (heterocycle)oxy group, as defined above, attached to the parent molecular group through an alkylene group, as defined above.

The term "hydroxy" or "hydroxyl," as used herein, refers to —OH.

The term "hydroxyalkyl," as used herein, refers to an alkyl group, as defined above, substituted by one, two, or three hydroxyl groups.

The term "nitro," as used herein, refers to —NO$_2$.

The term "nitrogen protecting group," as used herein, refers to groups intended to protect an amino group against undesirable reactions during synthetic procedures. Commonly used nitrogen protecting groups are disclosed in Greene, *Protective Groups In Organic Synthesis*, (John Wiley & Sons, New York (1981). Preferred nitrogen protecting groups are formyl, acetyl, benzoyl, pivaloyl, tert-butylacetyl, phenylsulfonyl, benzyl, tert-butyloxycarbonyl (Boc), and benzyloxycarbonyl (Cbz).

The term "perfluoroalkoxy," as used herein, refers to a perfluoroalkyl group, as defined below, attached to the parent molecular group through an oxygen atom.

The term "perfluoroalkyl," as used herein, refers to an alkyl group, as defined above, wherein each hydrogen radical bound to the alkyl group has been replaced by a fluoride radical. Examples of perfluoroalkyl groups include trifluoromethyl, pentafluoroethyl, and the like.

The term "pharmaceutically acceptable ester," as used herein, refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyates, acrylates and ethylsuccinates.

The term "pharmaceutically acceptable prodrugs," as used herein, refers to those V prodrugs of the compounds of the present invention which are, within the scope of sound medical judgement, suitable for use in contact with with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

The term "pharmaceutically acceptable salt," as used herein, refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in *J. Pharmaceutical Sciences*, 1977, 66:1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations including ammonium, tetramethylammonium, tetraethylammonium, methylamine, dimethylamine, trimethylamine, triethylamine, ethylamine, and the like.

The term "phenoxy," as used herein, refers to a phenyl group, as defined below, attached to the parent molecular moiety through an oxygen atom.

The term "phenoxyalkyl," as used herein, refers to a phenoxy group, as defined above, attached to the parent molecular moiety through an alkyl group, as defined above.

The term "phenyl," as used herein, refers to a monovalent radical derived from benzene by the removal of one hydrogen atom. Phenyl groups of the invention can be optionally substituted.

The term "phenylalkoxy," as used herein, represents a phenyl group, as defined above, attached to the parent molecular group through an alkoxy group, as defined above.

The term "phenylalkyl," as used herein, refers to a phenyl group, as defined above, attached to the parent molecular moiety through an alkyl group, as defined above.

The term "piperidineneyl," as used herein, refers to a divalent piperidine group derived from piperidine by the removal of hydrogens from any two positions on the ring. Piperidineneyl groups of the invention can be optionally substituted.

The term "sulfinylalkyl," as used herein, refers to an alkyl group, as defined above, attached to the parent molecular moiety through an —S(O)— group.

The term "sulfonylalkyl," as used herein, refers to an alkyl group, as defined above, attached to the parent molecular moiety through an —$SO_2$— group.

The term "thioalkoxy," as used herein, refers to an alkyl group, as defined above, attached to the parent molecular moiety through a sulfur atom.

The term "thioalkoxyalkyl," as used herein, refers to a thioalkoxy group, as defined above, attached to the parent molecular moiety through an alkyl group, as defined above.

Asymmetric centers may exist in the compounds of the present invention. The present invention contemplates the various stereoisomers and mixtures thereof. Individual stereoisomers of compounds of the present invention are made by synthesis from starting materials containing the chiral centers or by preparation of mixtures of enantiomeric products followed by separation as, for example, by conversion to a mixture of diastereomers followed by separation by recrystallization or chromatographic techniques, or by direct separation of the optical enantiomers on chiral chromatographic columns. Starting compounds of particular stereochemistry are either commercially available or are made by the methods detailed below and resolved by techniques well known in the organic chemical arts.

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection or for rectal administration.

The pharmaceutical compositions of this invention can be administered to humans and other animals orally, rectally, parenterally, intracistemally, intravaginally, intraperitoneally or topically (such as powders, ointments or drops), bucally or as an oral or nasal spray. The term "parenteral" administration, as used herein, refers to modes of administration which include intravenous, intramuscular, intraperitoneal, intrastemal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants.

These compositions may also contain adjuvants such as preservative, wetting agents, emulsifying agents and dispersing agents. Prevention of the action of microorganisms may be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form may be brought about by the inclusion of agents (such as aluminum monostearate and gelatin) which delay absorption.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable media just prior to use.

Solid dosage forms for oral administration include capsules, tablets, pills, powders and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and may also be of a composition such that they release the active ingredient(s) only, or preferentially, in a certain part of the intestinal tract, optionally or in delayed fashion. Examples of embedding compositions which can be used include polymeric substances and waxes.

The active compounds may also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perftuming agents.

Suspensions, in addition to the active compounds, may contain suspending agents' such as ethoxylated isostearyl alcohols, polyoxyethylene sorbitol and sorbitan esters, microcrystalline cellulose, aluminum metahydroxide, bentonite, agar-agar, and tragacanth and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants which may be required. Opthalmic formulations, eye ointments, powders and solutions are also contemplated as being within the scope of this invention. Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about one to about 50, more preferably of about five to about 20 mg, of active compound per kilogram of body weight per day when administered orally to a mammalian patient. If desired, the effective daily dose may be divided into multiple doses for purposes of administration, e.g. two to four separate doses per day.

Determination of Stromelysin Inhibition

The efficacy of the compounds of this invention as matrix metalloproteinase inhibitors was determined by measuring the inhibition of stromelysin. The inhibition of stromelysin by the compounds of this invention was determined as follows: recombinant truncated stromelysin (human sequence) produced in E. coli was prepared by expression and purification of the protein as described by Ye et al, Biochemistry, 1992, 31, 11231–11235. The $IC_{50}$ values were determined as described in Steiman et al, Bioorganic and Medicinal Chemistry Letters, (1998), 8, 2087–2092 (footnote 13). The compounds of this invention inhibited stromelysin as shown by the data for representative examples in Table 1.

TABLE 1

| Example | $IC_{50}$ ($\mu$M) |
|---|---|
| 1 | 0.64 |
| 6 | 0.67 |
| 7 | 0.46 |
| 8 | 3.7 |
| 9 | 0.69 |
| 10 | 0.40 |
| 11 | 1.5 |
| 12 | 0.45 |
| 13 | 0.062 |

Thus the compounds of the invention inhibit MMP's and are useful for the treatment of diseases caused or exacerbated by MMP's.

Synthetic Methods

Abbreviations

Abbreviations which have been used in the descriptions of the schemes and the examples that follow are: Boc for tert-butyloxycarbonyl, CBZ for benzyloxycarbonyl, DMF for N,N-dimethylformamide, THF for tetrahydrofuran, EtOAc for ethyl acetate, EtOH for ethanol, MeOH for methanol, DEAD for diethylazodicarboxylate, HOAc for acetic acid, $Et_2O$ for diethylether, M for molar, and THP for tetrahydropyranyl.

Chemistry

The compounds and processes of the present invention will be better understood in connection with the following examples, which are intended as an illustration of and not a limitation upon the scope of the invention. The compounds of this invention may be prepared by a variety of synthetic routes. Representative procedures are outlined in Schemes 1–7 where Bn is a benzyl group, tBu is a tert-butyl group and $Ar^1$, $Ar^2$, X, and Y are previously defined. It will be readily apparent to one of ordinary skill in the art reviewing the synthetic routes depicted below that other compounds within formula I can be synthesized by substitution of appropriate reactants and reagents in the synthetic schemes below.

Scheme 1

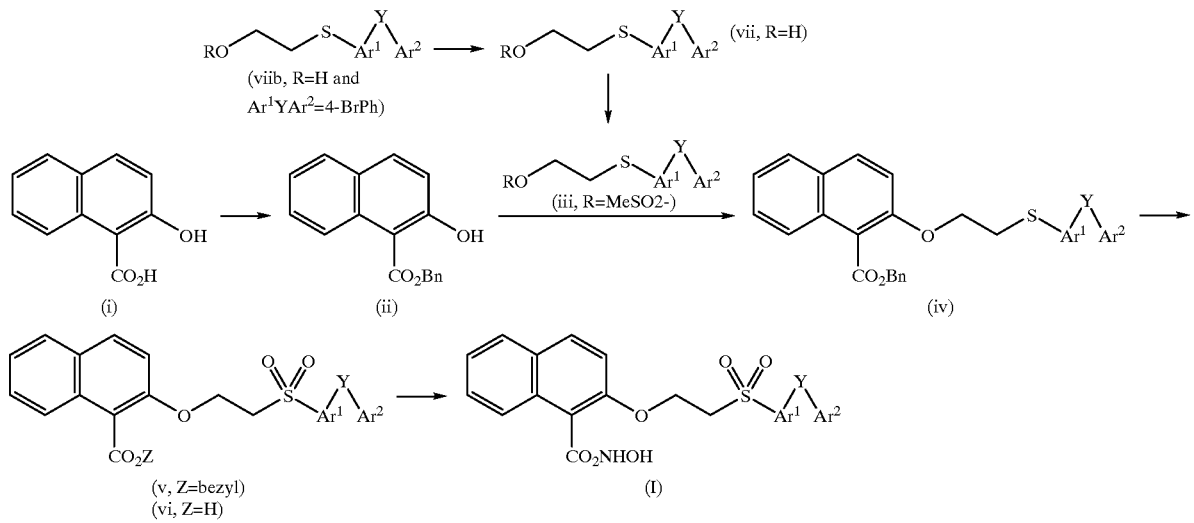

Scheme 1 shows a general synthetic route to compounds of formula I. Reaction of 2-hydroxy-1-napthoic acid with benzyl bromide and cesium carbonate in DMF provided the benzyl ester (ii). The ester (ii) was reacted with sodium hydride and compound (iii) to provide (iv). Intermediate (iv) was oxidized with 3-chloroperoxybenzoic acid in methylene chloride to provide sulfone (v). The benzyl group was removed by reacting (v) with hydrogen over 10% palladium-carbon in acetic acid-THF to provide the carboxylic acid (vi). The acid (vi) was reacted with oxalyl chloride in DMF, and the resulting acid chloride was then reacted with hydroxylamine hydrochloride and triethylamine to provide a compound of formula I. Intermediate (iii) was prepared by the following reaction sequence also shown in Scheme 1: reaction of 4-bromothiophenol with sodium hydride and bromoethanol in DMF provided compound (viib). Compound (viib) was reacted with 4-chlorophenylboronic acid, cesium fluoride, and tetrakis(triphenylphosphine)-palladium(O) in DMF to provide (vii). Reaction of (vii) with methanesulfonyl chloride and triethylamine in dichloromethane provided (iii).

Scheme 2

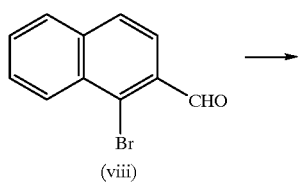

-continued

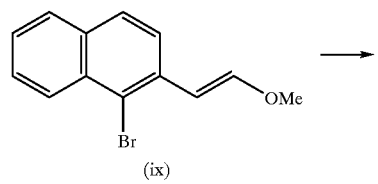

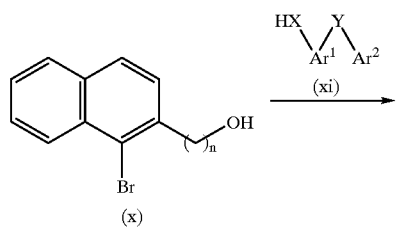

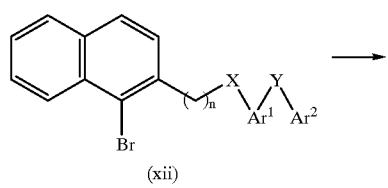

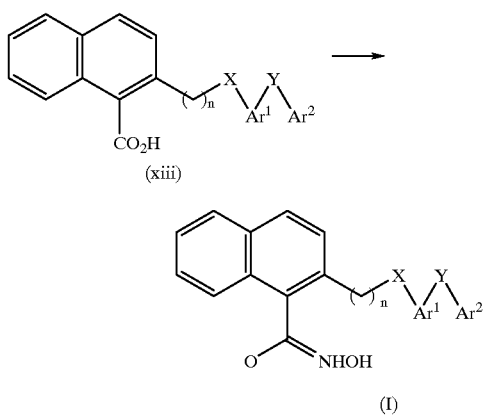

Scheme 2 also shows a general synthetic route to compounds of formula I. (Methoxymethyl)triphenyl phosphonium ylide was reacted with 1-bromo-2-naphthaldehyde to provide (ix). Intermediate (ix) was reacted with para-toluenesulfonic acid in aqueous dioxane to give an aldehyde whixh was reduced with sodium borohydride to provide the corresponding alcohol ((x), n=2) The alcohol was reacted with 4-chloro-z4'-hydroxybiphenyl, triphenyl, phosphine and diisobutylcarbodiimide to provide bromo ether (xii). Compound (xii) was reacted with n-butyllithium followed by carbon dioxide to provide the carboxylic acid (xiii). The carboxylic acid was converted to a compound of formula I following the procedure outlined in Scheme 1.

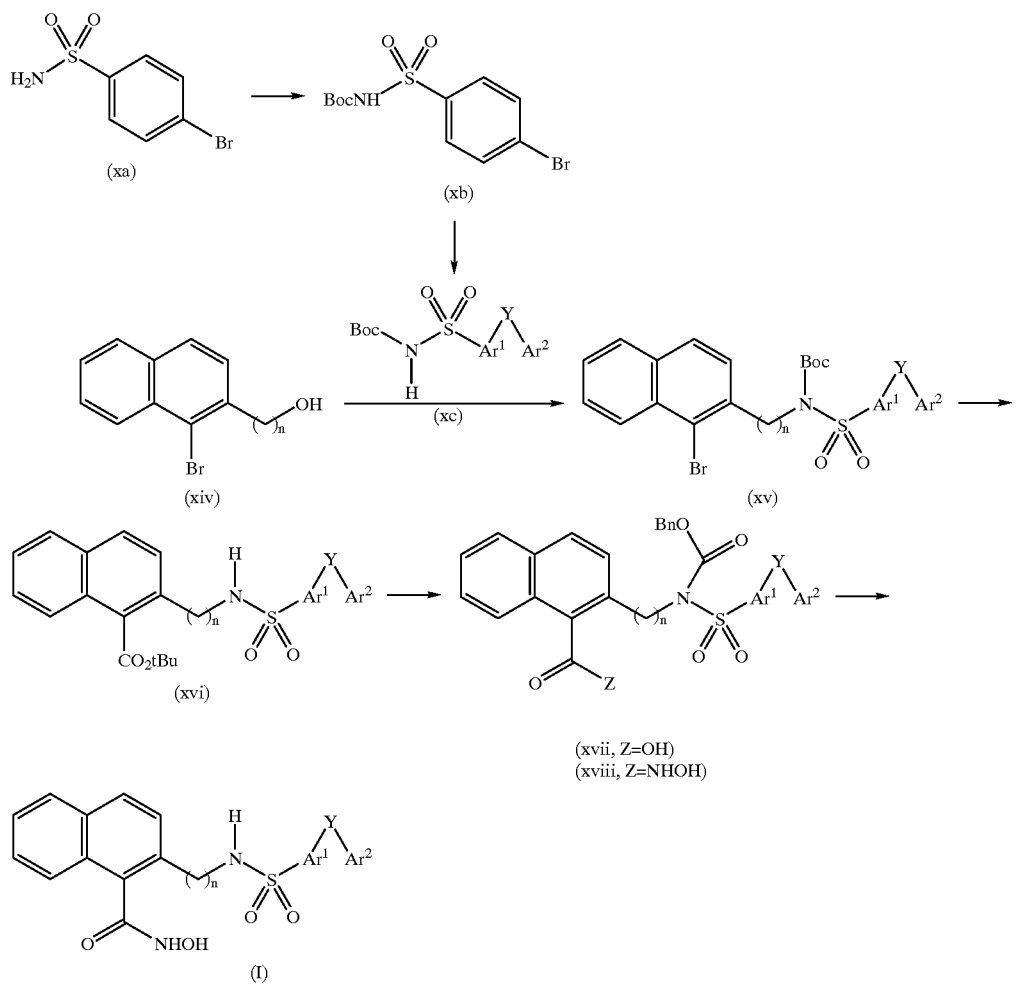

Scheme 3 also shows a general synthetic route to compounds of formula I. Reaction of 1-bromo-2-naphthaldehyde with sodium borohydride provided 1-bromo-2-naphthalenemethanol (xiv). Alcohol (xiv) was reacted with BOC-protected sulfonamide (xc), triphenylphosphine and diethyl azodicarboxylate to provide sulfonamide (xv). The sulfonamide was reacted with tert-butyllithium at a temperature between about -90° C. and about 10° C. in THF to provide (xvi). The nitrogen of compound (xvi) was protected as the benzyl carbamate by treating (xvi) with sodium hydride and benzylchloroformate, and the tert-butyl ester was then hydrolyzed with trifluoroacetic acid to provide carboxylic acid (xvii). The carboxylic acid (xvii) was converted to the hydroxamate (xviii) following the procedure outlined in Scheme 1. Hydrogenation of (xvii) in the presence of a palladium catalyst provided a compound of formula I.

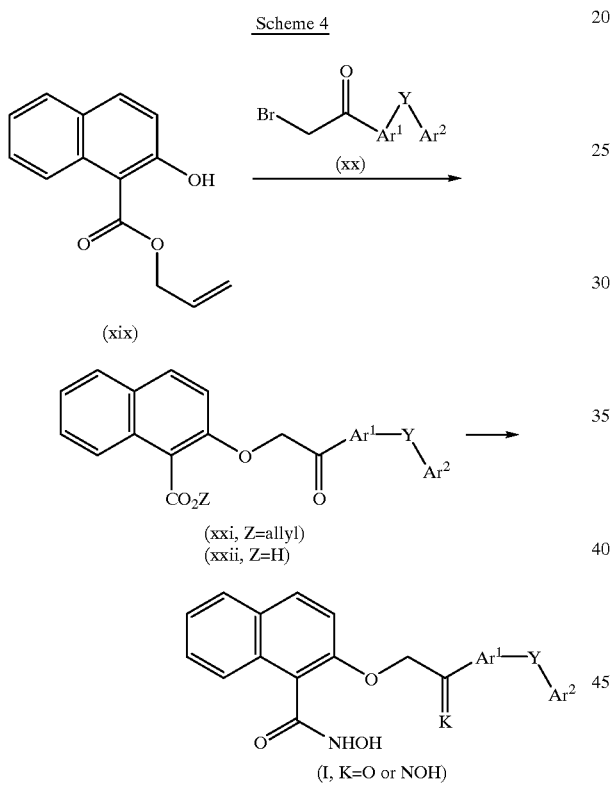

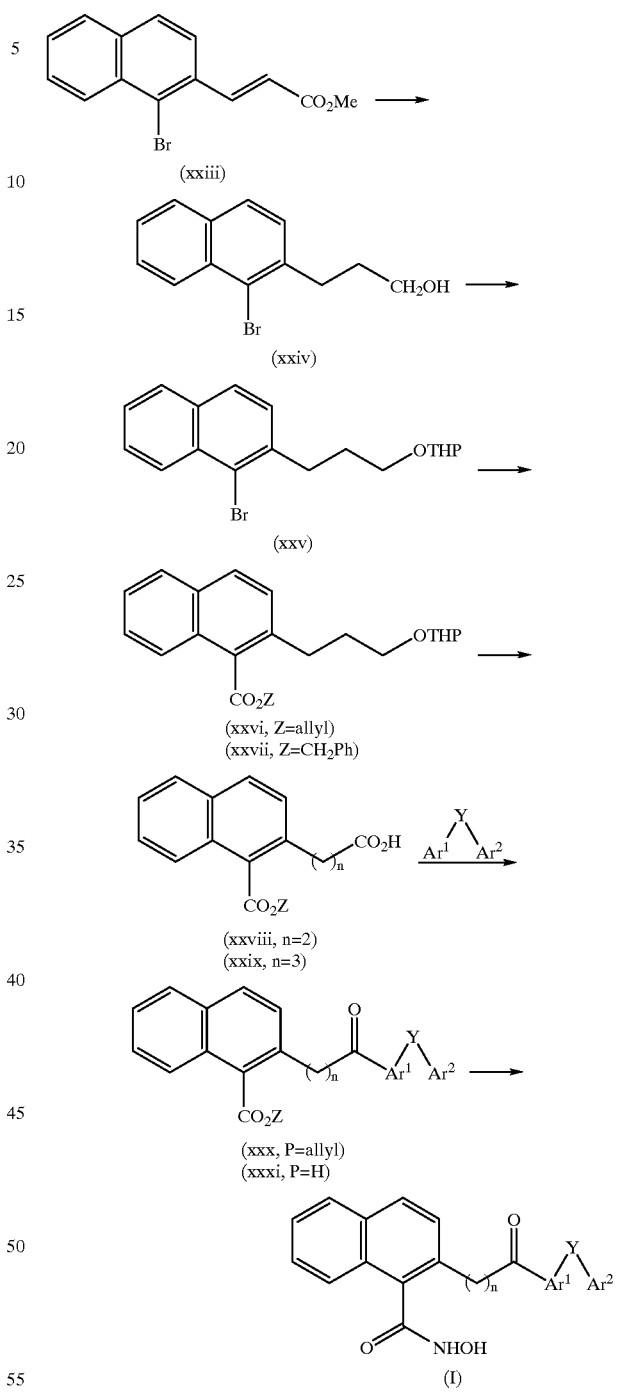

Scheme 4 also shows a general synthetic route to compounds of formula I. 2-Hydroxy-1-naphthoic acid was reacted with cesium carbonate and allyl bromide to provide hydroxy ester (xix). The hydroxy ester was reacted with sodium hydride and an a-halo ketone such as 1-(2-bromoethanone)-4-(4-chlorophenyl)benzene (xx) to provide keto ester (xxi). The carboxylic ester was converted to the acid (xxii) by reaction with tetrakis(triphenylphosphine) palladium(0) and pyrolidine in aquous dioxane. The acid (xxii) was reacted with oxalyl chloride in DMF, and the resulting acid chloride was reacted with hydroxylamine hydrochloride and triethylamine for 2 hours to provied a compound of formula I where K is O or reacted for 24 hours to provide a compound of formula I where K is NOH.

Scheme 5 also shows a general synthetic route to compounds of formula I. Wittig reaction of methyl (triphenylphosphoranylidene) acetate with 1-bromo-2-naphthaldehyde gave the unsaturated ester (xxiii). The ester was then reduced with a metal hydride reagent such as sodium borohydride and then hydrogenated to provide the alcohol (xxiv). Protection of the alcohol as the THP ether provided (xxv). Metal-halogen exchange of (xxv) using n-butyllithium followed by reaction with carbon dioxide and protection of the resulting carboxylic acid as the allyl ester provided (xxvi). Hydrolysis of the THP protecting group followed by oxidation of the resulting alcohol provided (xxviii). Reaction of carboxylic acid (xxviii) with thionyl chloride followed by reaction of the resulting acid chloride with the appropriate biphenyl compound and aluminum chloride provided (xxx). The protecting group Z of carboxylic acid (xxx) was removed as outlined in Scheme 4 to provide (xxxi). The carboxylic acid (xxxi) was converted to compound of formula I following the procedure outlined in Scheme 1. To produce a compound of formula I where n=3, the carbon chain attached to the carboxylic acid group in compound (xxviii) was extended using a standard homologation sequence such as the Arndt-Eistert procedure to provide (xxix). Compound (xxix) was subjected to the same reaction sequence as described above for conversion of (xxviii) to a compound of formula I.

Scheme 6

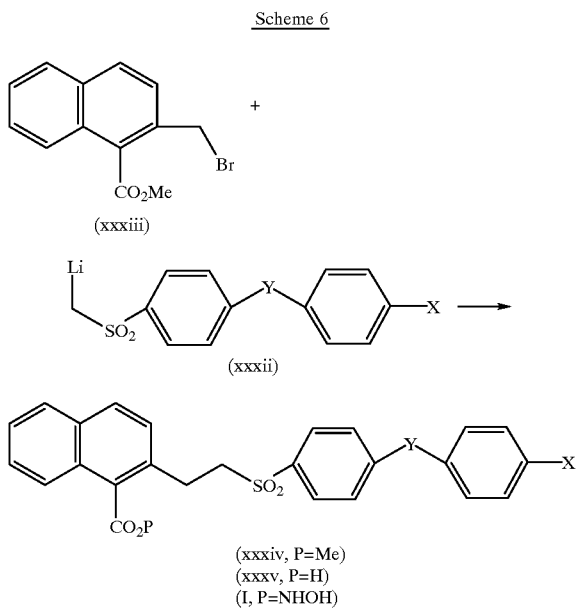

(xxxiv, P=Me)
(xxxv, P=H)
(I, P=NHOH)

Scheme 6 also shows a general synthetic route to compounds of formula I. Reaction of 4-chloro-4'-methylsulfone biphenyl with n-butyllithium at a temperature between about −90° C. and about −10° C. provided the lithio compound (xxxii). Reaction of (xxxii) with methyl 2-(bromomethyl)-1-naphthoate (xxxiii) provided the naphthylene biphenyl compound (xxxiv). Hydrolysis of the ester with lithium hydroxide provided carboxylic acid (xxxv). The carboxylic acid (xxxv) was converted to a compound of formula I following the procedure outlined in Scheme 1.

Scheme 7

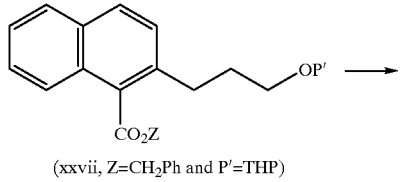

(xxvii, Z=CH₂Ph and P'=THP)
(xxxvi, Z=CH₂Ph and P'=H)

-continued

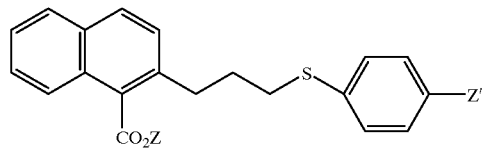

(xxxviii, Z=CH₂Ph and Z'=Br)
(xxxix, Z=CH₂Ph and Z'=4-methoxyphenyl)

Scheme 7 also shows a general synthetic route to compounds of formula I. Protected alcohol (xxv) (see Scheme 5) was converted to (xxvii) using the same reaction sequence used to make (xxvi) (see Scheme 5) except substituting benzyl bromide for allyl bromide. Reaction of (xxvii) with para-toluenesulfonic acid provided alcohol (xxxvi). Reaction of (xxxvi) with 1,1'-(azodicarbonyl)bispiperidine (ADDP), tributylphosphine, and 4-bromothiophene provided (xxxviii). Reaction of (xxxviii) with 4-methoxybenzene boronic acid, cesium fluoride, and tetrakis(triphenylphosphine)palladium(0) in a polar solvent such as DMF provided (xxxix). Conversion of (xxxix) to a compound of formula I proceeded via the same pathway described for the conversion of (iv) to a compound of formula I as described in Scheme 1.

EXAMPLE 1

2-[2-[(4'-chloro[1,1'-biphenvyl]-4-vl)oxy]eyl]-N-hydroxy-1-naphthalenecarboxamide

EXAMPLE 1A 1-bromo-2-(2-methoxyethenyl)naphthalene

A solution of (methoxymethyl)triphenyl phosphonium chloride (32.0 g, 93.3 mmol) in THF (100 mL) at −78° C. was treated with potassium tert-butoxide (9.90 g, 88.1 mmol), stirred cold for 1 hour, treated with a solution of 1-bromo-2-naphthaldehyde (12.1 g, 51.7 mmol) (commercially available from TCI America) in THF (75 mL) over 15 minutes, stirred for 16 hours at room temperature, treated with aqueous ammonium chloride (200 mL) and extracted with ethyl acetate. The ethyl acetate was washed with brine, dried (MgSO₄), filtered, and concentrated to an oil. The oil was purified on silica gel with a gradient of 2% to 5% ethyl acetate/hexanes to provide 11.8 g (87%) of the desired compound.

MS (DCI/NH₃) m/e 263 (M+H)⁺.

EXAMPLE 1B 1-bromo-2-naphthaleneacetaldehyde

A solution of Example 1A (11.8 g, 45.0 mmol) in 20% aqueous dioxane (150 mL), was treated with p-toluene sulfonic acid (1.71 g, 9.00 mmol), heated to reflux for 2 hours, cooled to room temperature and concentrated. The residue was dissolved in diethyl ether, washed with aqueous NaHCO₃ and brine, dried (MgSO₄), filtered, and concentrated to an oil. The oil was purified on silica gel with a gradient of 2% to 5% ethyl acetate/hexanes to provide 2.07 g (18%) of the desired compound.

MS (DCI/NH₃) m/e 249 (M+H)⁺.

EXAMPLE 1C 1-bromo-2-naphthaleneethanol

A solution of Example 1B (2.07 g, 8.35 mmol) in methyl alcohol (15 mL) was treated with sodium borohydride (0.47 g, 12.5 mmol), stirred for 2 hours, quenched by addition to 1.0 M $H_3PO_4$, and concentrated. The residue was dissolved in ethyl acetate, washed with water and brine, dried ($MgSO_4$), filtered, and concentrated to provide 1.52 g (73%) of the desired compound. MS ($DCI/NH_3$) m/e 252 $(M+H)^+$.

EXAMPLE 1D 1-bromo-2-[2-[(4'-chloro [1,1'-biphenyl]-4-yl)oxy] ethyl]naphthalene A solution of Example 1C (1.51 g, 6.04 mmol), 4 chloro-4'-hydroxybiphenyl (1.35 g, 6.64 mmol), triphenylphosphine (2.37 g, 9.06 mmol), and diisobutylcarbodiimide (1.78 mL, 9.06 mmol) in THF (10 mL) was stirred for 24 hours, concentrated, and purified on silica gel with 10% ethyl acetate/hexanes to provide 0.33 g (28%) of the desired compound.

MS ($DCI/NH_3$) m/e 456 $(M+NH_4)^+$.

EXAMPLE 1E

2-[2-[(4'-chloro[1,1'-biphenyl]-4-yl)oxy]ethyl]-1-naphthalenecarboxylic Acid

A solution of Example 1D (0.33 g, 0.82 mmol) in THF (10 mL) at −78° C. was treated with n-butyllithium (0.37 mL, 0.92 mmol), stirred cold for 15 minutes, treated with gaseous carbon dioxide, stirred cold 15 minutes, quenched into 0.5 M aqueous HCl, and extracted with ethyl acetate. The ethyl acetate was washed with water and brine, dried ($MgSO_4$), filtered, and concentrated to provide 0.33 g (89%) of the desired compound.

MS ($DCI/NH_3$) m/e 420 $(M+NH_4)^+$.

EXAMPLE 1F

2-[2-[(4'-chloro[1,1'-biphenyl]-4-yl)oxy]ethyl]-1-naphthalenecarboxamide

A solution of Example 1E (0.32 g, 0.80 mmol) in $CH_2Cl_2$ (15 mL) containing DMF (0.05 mL) at 0° C. was treated with oxalyl chloride (0.08 mL, 0.96 mmol), stirred at room temperature for 15 minutes. The resulting solution was transferred to a solution of hydroxylamine hydrochloride (0.28 g, 4.0 mmol) and triethylamine (0.56 mL, 4.0 mmol) in 10:1 THF/water (50 mL) at 0° C., stirred for 2 hours and concentrated. The residue was dissolved in ethyl acetate, washed with 0.5 M HCl, water and brine, dried ($MgSO_4$), filtered, and concentrated to a white solid. The solid was crystallized from ethyl acetate/hexanes to provide 0.15 g (46%) of the desired compound.

MS ($DCI/NH_3$) m/e 417 $(M+H)^+$;

$^1$H NMR (300 MHz, DMSO-$d_6$) δ 3.20 (t, 2H), 4.28 (t, 2H), 7.03 (d, 2H), 7.45 (d, 2H), 7.62 (m, 7H), 7.80 (d, 1H), 7.93 (m, 2H), 9.37 (s, 1H), 11.08 (s, 1H);

Anal. calc'd for $C_{25}H_{20}NO_3Cl.0.5\ H_2O$: C, 70.34; H, 4.96; N, 3.28. Found: C, 70.48; H, 4.87; N, 3.29.

EXAMPLE 2

2-[2-[(4'-chloro[1,1'-biphenyl]-3-yl)oxy]ethyl]-N-hydroxy-1-naphthalenecarboxamide Example 1C was prepared as described in examples 1D, 1E and 1F, except using 4-chloro-3'-hydroxybiphenyl in place of 4-chloro-4'-hydroxybiphenyl in Example 1D.

MS ($DCI/NH_3$) m/e 417 $(M+H)^+$;

Anal. calc'd for $C_{25}\ H_{20}NO_3Cl.0.25\ H_2O$: C, 70.34; H, 4.96; N, 3.28. Found: C, 70.58; H, 5.11; N, 3.40.

EXAMPLE 3

2-[3-[(4'-chloro[1,1'-biphenyl]-4-yl)oxy]propyl]-N-hydroxy-1-naphthalenecarboxamide

EXAMPLE 3A

Methyl 3-(1-bromo-2-naphthalenyl)-2-propenoate

A solution of 1-bromo-2-naphthaldehyde (6.12 g, 26.1 mmol) (TCI America) in THF (75 mL) was treated with methyl(triphenylphasphoranylidene)acetate (9.62 g, 28.7 mmol), stirred for 16 hours, diluted with aqueous ammonium chloride, and extracted with ethyl acetate. The ethyl acetate was washed with water and brine, dried ($MgSO_4$), filtered, and concentrated to provide 7.20 g (95%) of the desired compound.

MS ($DCI/NH_3$) m/e 291 $(M+H)^+$.

EXAMPLE 3B 3-(1-bromo-2-naphthalenyl)-2-propenoic Acid

A solution of Example 3A (6.12 g, 26.1 mmol) and lithium hydroxide (5.48 g, 130 mmol) in 40% aqueous THF (75 mL) was stirred for 16 hours, diluted with 0.5 M HCl, and extracted with ethyl acetate. The ethyl acetate was washed with brine, dried ($MgSO_4$), filtered, and concentrated to provide 4.66 g (64%) of the desired compound.

MS ($APCI^+$) m/e 279 $(M+H)^+$.

EXAMPLE 3C 3-(1-bromo-2-naphthalenyl)-2-propenol

To a solution of Example 3B (4.66 g, 16.9 mmol) and triethylamine (2.70 mL, 19.4 mmol) in THF (25 mL) at −20° C. was added methyl chloroformate (1.60 mL, 10.3 mmol), and the resulting solution was stirred for 15 minutes. This solution was then added to sodium borohydride (1.92 g, 50.6 mmol) in water (10 mL) at 0° C., stirred at room temperature for 2 hours, acidified with 0.5 M $H_3PO_4$, and extracted with ethyl acetate. The ethyl acetate was washed with water, brine, dried ($MgSO_4$), filtered, and concentrated to provide 2.10 g (47%) of the desired compound.

MS ($APCI^+$) m/e 263 $(M+H)^+$.

EXAMPLE 3D 1-bromo-2-(3-chloro-1-propenyl)naphthalene

A solution of Example 3C (0.85 g, 3.24 mmol), collidine (0.94 mL, 7.13 mmol) and lithium chloride (0.21 g, 4.97 mmol) in DMF (10 mL) at 0° C. was treated with methanesulfonyl chloride (0.38 mL, 4.87 mmol), stirred 16 hours at room temperature, poured into aqueous ammonium chloride, and extracted with ethyl acetate. The ethyl acetate was washed with water, brine, dried ($MgSO_4$), filtered, concentrated, and purified on silica gel with 3% ethyl acetate/hexanes to provide 0.35 g (38%) of the desired compound.

MS ($APCI^-$) m/e 279$(M+H)^-$

EXAMPLE 3E 1-bromo-2-[3-(4'-Chloro-biphenyl-4-yloxy)-propenyl]-naphthalene

A solution of 4,4'-chlorobiphenol (0.31 g, 1.5 mmol) in DMF (5 mL) was treated with sodium hydride (0.06 g, 1.5 mmol), stirred for 30 minutes, treated with Example 3D, stirred for 16 hours, treated with aqueous ammonium chloride, and extracted with ethyl acetate. The ethyl acetate was washed with water, brine, dried ($MgSO_4$), filtered, and concentrated to provide 0.315 g (56%) of the desired compound.

MS ($APCI^+$) m/e 449$(M+H)^+$.

EXAMPLE 3F

2-[3-[(4'-chloro[1,1'-biphenyl]-4-yl)oxy]-1-propenyl]-1-naphthalenecarboxylic Acid Example 3E was prepared according to the procedure described in Example 1E to provide the desired compound.

MS (DCI/NH$_3$) m/e 432 (M+NH$_4$)$^+$.

EXAMPLE 3G

2-[3-[(4'-chloro[1,1'-biphenyl]-4-yl)oxy]propyl]-1-naphthalenecarboxylic Acid

A mixture of a solution of Example 3F (0.13 g, 0.31 mmol) in methanol containing 10% acetic acid and 10% Palladium on carbon (0.025 g) was stirred under an atmosphere of hydrogen for 16 hours, filtered, and concentrated to provide 0.12 g (91%) of the desired compound.

MS (DCI/NH$_3$) m/e 434 (M+NH$_4$)$^+$.

EXAMPLE 3H

2-[3-[(4'-chloro[1,1'-biphenyl]-4-yl)oxy]propyl]-N-hydroxy-1-naphthalenecarboxamide Example 3G was prepared according to the procedure described in Example IF to provide the desired compound.

MS (DCI/NH$_3$) m/e 432 (M+H)$^+$;
$^1$H NMR (300 MHz, DMSO-d$_6$) δ 2.14 (m, 2H), 2.92 (m, 2H), 4.04 (m, 2H), 7.02 (d, 2H), 7.48 (m, 4H), 7.61 (m, 5H), 7.78 (m, 1H), 7.93 (m, 2H), 9.29 (s, 1H), 11.10 (s, 1H);
Anal. calc'd for C$_{26}$H$_{22}$NO$_3$Cl: C, 72.16; H, 5.12; N, 3.23. Found: C, 71.90; H, 5.50; N, 3.14.

EXAMPLE 4

2-[2-(4'-chloro[1,1'-biphenyl]-4-yl)-2-oxoethoxy]-N-hydroxy-1-naphthalenecarboxamide

EXAMPLE 4A 2-propenyl 2-[2-(4'-chloro[1,1'-biphenvyl]-4-yl)-2-oxoethox]-1-naphthalenecarboxylate A solution of 2-hydroxy-1-allylnaphthyl carboxylate (1.55 g, 6.8 mmol) in DMF (8 mL) at 0° C. was treated with sodium hydride (0.30 g, 7.8 mmol), stirred 30 minutes, treated with 1-(2-bromoethanone)-4-(4-chlorophenyl)-benzene (2.30 g, 7.80 mmol) (preparation described in WO/9615096, p.75) and stirred for 24 hours. The resulting mixture was treated with aqueous ammonium chloride and extracted with ethyl acetate. The ethyl acetate was washed with water and brine, dried (MgSO$_4$), filtered, and the resulting oil purified on silica gel using 20% ethyl acetate/hexanes to provide 1.24 g (40%) of the desired compound.

MS (DCI/NH$_3$) m/e 457 (M+H)$^+$.

EXAMPLE 4B

2-[2-(4'-chloro[1,1'-biphenyl]-4-yl)-2-oxoethoxy]-1-naphthalenecarboxylic Acid

A solution of Example 4A (1.24 g, 2.71 mmol), tetrakis(triphenylphosphine)-palladium(0) (0.16 g, 0.14 mmol), pyrrolidine (0.50 mL, 6.0 mmol) in 10% aqueous dioxane (10 mL) was stirred for 16 hours, diluted with ethyl acetate, washed with 0.5 M HCl, water and brine, dried (MgSO$_4$), filtered, and concentrated. The residue was crystallized from ethyl acetate/hexanes to provide 0.19 g (16%) of the desired compound.

MS (DCI/NH$_3$) m/e 434 (M+NH$_4$)$^+$.

EXAMPLE 4C

2-[2-(4'-Chloro-biphenyl-4-yl)-2-oxo-ethoxy]-naphthalene-1-carboxylic Acid Hydroxyamide Example 4B was prepared according to the procedure described in Example 1F to provide the desired compound.

MS (APCI$^+$) m/e 431 (M+H)$^+$;
$^1$H NMR (300 MHz, DMSO-d$_6$) δ 5.81 (s, 2H), 7.38 (m, 2H), 7.57 (m, 4H), 7.84 (m, 6H), 8.23 (m, 2H), 9.20 (d, 1H), 10.87 (d, 1H);
Anal. calc'd for C$_{26}$H$_{22}$NO$_3$Cl: C, 68.10; H, 4.34; N, 3.18. Found: C, 68.40; H, 4.12; N, 3.16.

EXAMPLE 5

2-[2-(4'-chloro[1,1'-biphenyl]-4-yl)-2-(hydroxyimino)ethoxy]-N-hydroxy-1-naphthalenecarboxamide A solution of Example 4B (0.17 g, 0.41 mmol) in CH$_2$Cl$_2$ (15 mL) containing DMF (0.05 mL) at 0° C. was treated with oxalyl chloride (0.05 mL, 0.49 mmol), and stirred for 15 minutes. The mixture was transferred to a solution of hydroxylamine hydrochloride (0.14 g, 2.0 mmol) and triethylamine (0.29 mL, 2.0 mmol) in 10:1 THF/water (30 mL) at 0° C., stirred for 24 hours at room temperature, and concentrated. The residue was dissolved in ethyl acetate, washed with water and brine, dried (MgSO$_4$), filtered, and concentrated to provide a white solid. Recrystallization from ethyl acetate/hexanes provided 0.078 g (42%) of the desired compound.

MS (DCI/NH$_3$) m/e 447 (M+H)$^+$;
$^1$H NMR (300 MHz, DMSO-d$_6$) δ 5.80 (s, 2H), 7.40 (m, 2H), 7.58 (m, 3H), 7.82 (m, 8H), 8.23 (m, 2H), 9.20 (s, 1H), 10.84 (s, 1H);
Anal. calc'd for C$_{25}$H$_{19}$N$_2$O$_3$Cl: C, 69.68; H, 4.44; N, 6.50. Found: C, 69.54; H, 4.23; N, 6.34.

EXAMPLE 6

2-[[2-(4'-chloro[1,1'-biphenyl]-4-yl)sulfonyl]ethoxy]-N-hydroxy-1-naphthalenecarboxamide

EXAMPLE 6A phenylmethyl 2-hydroxy-1-naphthalenecarboxylate

A solution of 2-hydroxy-1-carboxynaphthalene (4.70 g, 25.0 mmol) and 20% cesium carbonate (20.3 mL, 12.5 mmol) in methanol (20 mL) was striped to dryness, dissolved in DMF (10 mL), treated with benzyl bromide (2.67 mL, 22.5 mmoL), stirred for 20 hours, diluted with brine, and extracted with ethyl acetate. The ethyl acetate was washed with water, 1 M NaOH, water and brine, dried (MgSO$_4$), filtered, and concentrated to provide 3.98 g (57%) of the desired compound.

MS (DCI/NH$_3$) mle 279 (M+H)$^+$.

EXAMPLE 6B

2-[(4-bromophenyl)thio]ethanol

A solution of bromothiophenol (4.72 g, 25.0 mmol) in DMF (20 mL) was treated with sodium hydride (1.10 g, 27.4 mmol), stirred for 30 minutes, treated with bromoethanol (1.95 mL, 27.4 mmol), stirred for 20 hours, treated with aqueous ammonium chloride, and extracted with ethyl acetate. The organic layer was washed with water and brine, dried (MgSO$_4$), filtered, and concentrated. The residue was purified on 9silica gel with 30% ethyl acetate/hexanes to provide 5.06 g (87%) of the desired compound.

MS (DCI/NH$_3$) m/e 232 (M+H)$^+$.

EXAMPLE 6C

2-[(4'-chloro[1,1'-biphenyl]-4-yl)thio]ethanol

A solution of Example 6B (2.77 g, 12.0 mmol), 4-chlorophenylboronic acid (2.06 g, 13.2 mmol), cesium fluoride (5.45 g, 35.9 mmol), and tetrakis(triphenylphosphine)palladium(0) (0.69 g, 0.60 mmol) in DME (75 mL) was heated to reflux for 16 hours, concentrated, and purified on silica gel with 30% ethyl acetate/hexanes to provide 2.87 g (90%) of the desired compound.

MS (DCI/NH$_3$) m/e 265 (M+H)$^+$.

EXAMPLE 6D

Phenylmethyl 2-[2-[(4'-chloro[1,1'-biphenyl]-4-yl)thio]ethoxy]-1-naphthalenecarboxylate A solution of Example 6C (0.50 g, 1.89 mmol) and triethylamine (0.39 mL, 2.84 mmol) in CH$_2$Cl$_2$ (10 mL) at 0° C. was treated with methanesulfonyl chloride (0.18 mL, 2.27 mmol). After 1 hour, the reaction mixture was washed with 0.5 M HCl, water and brine, dried (MgSO$_4$), filtered, and concentrated. The residue was dissolved in DMF (1 mL), added to a solution of Example 6A (0.58g, 2.08 mmol) and sodium hydride (0.087 g, 2.20 mmol) in DMF (6 mL) at 0° C. The mixture was heated to 50° C. for 4 hours, cooled, washed with brine, dried (MgSO$_4$), filtered, concentrated, and purified on silica gel using 20% ethyl acetate/hexanes to provide 0.49 g (50%) of the desired compound.

MS (DCI/NH$_3$) m/e 525 (M+H)$^+$.

EXAMPLE 6E

Phenylmethyl 2-[2-[(4'-chloro[1,1'-biphenyl]-4-yl)sulfonyl ethoxy]-1-naphthalenecarboxylate A solution of Example 6D (0.42 g, 0.75 mmol) and 3-chloro peroxybenzoic acid (0.65 g, 3.76 mmol) in methylene chloride (50 mL) was heated at reflux for 16 hours, washed with aqueous sodium bisulfite, aqueous sodium bicarbonate, water and brine, dried (MgSO$_4$), filtered, and concentrated. Recrystallization from ethyl acetate/hexanes provided 0.18 g (43%) of the desired compound.

MS (DCI/NH$_3$) m/e 574 (M+NH$_4$)$^+$.

EXAMPLE 6F

2-[2-[(4'-chloro[1,1'-biphenyl]-4-yl)sulfony]ethoxy]-1-naphthalenecarboxylic acid A mixture of a solution of Example 6E (0.18 g, 0.32 mmol) in 20% acetic acid- THF and 10% palladium-carbon (0.050 g) was stirred at room temperature under an atmosphere of hydrogen for 20 hours, filtered, and concentrated to provide 0.086 g (58%) of the desired compound.

MS (DCI/NH$_3$) m/e 484 (M+NH$_4$)$^+$.

EXAMPLE 6G

2-[2-(4'-chloro[1,1'-biphenyl]-4-yl)sulfonyl]ethoxy]-N-hydroxy-1-naphthalenecarboxamide Example 6F was prepared according to the procedure described in Example 1F to provide the desired compound.

MS (DCI/NH$_3$) m/e 482 (M+H)$^+$;

$^1$H NMR(300 MHz, DMSO-d$_6$) δ 4.87 (m, 2H), 4.46 (m, 2H), 7.41 (m, 2H), 7.56 (m, 4H), 7.78 (m, 3H), 7.98 (m, 5H), 9.20 (s, 1H), 11.02 (s, 1H).

EXAMPLE 7

N-hydroxy-2-[2-[(4'-methoxy[1,1'-biphenyl]-4-vl)sulfonyl]ethoxy]-1-naphthalenecarboxamide

EXAMPLE 7A

Phenylmethyl 2-[2-[(4'-bromo[1,1'-biphenvyl]-4-yl)thio]ethoxy]-1-naphthalenecarboxylate A room temperature solution of 1,1'-(azodicarbonyl) dipiperidine) (ADDP) (0.684 g, 2.7 mmol) in benzene (6 mL) was treated with tributylphospine (0.695 mL, 2.7 mmol) and a solution of Example 6B (0.42 g, 1.80 mmol) in benzene (3 mL) and stirred for 5 minutes, followed by addition of Example 6A (0.503 g, 1.81 mmol). The resulting mixture was diluted with 3 mL of benzene, stirred for 45 minutes, and concentrated in vacuo. The residue was purified on silica gel using 10% ethyl acetate in hexanes to provide 0.62 g (70%) of the desired compound.

EXAMPLE 7B

Phenylmethyl 2-[2-[(4'-methoxy[1,1'-biphenyl]-4-yl)thio]ethoxy]-1-nayhthalenecarboxylate Example 7A was prepared as described in Example 6D, except using 4-methoxyphenylboronic acid in place of 4-chlorophenylboronic acid.

EXAMPLE 7C

N-hydroxy-2-[2-[(4'-methoxy[1,1'-biphenyl]-4-yl)thio]ethoxy]-1-naphthalenecarboxamide Example 7A was prepared according to the procedure described in examples 6E, 6F and 6G.

MS (DCI/NH$_3$) mle 478 (M+H)$^+$;

$^1$H NMR (300 MHz, DMSO-d$_6$) δ 4.87 (m, 2H), 4.46 (m, 2H), 3.80 (s, 3H), 7.41 (m, 2H), 7.56 (m, 4H), 7.78 (m, 3H), 7.98 (m, 5H), 9.20 (s, 1H), 11.02 (s, 1H).

EXAMPLE 8

2-[2-[(4'-chloro[1,1'-biphenyl]-4-yl)sulfonyl]ethyl]-N-hydroxy-1-naphthalenecarboxamide

EXAMPLE 8A

Methyl 2-[2-[(4'-chloro[1,1'-biphenyl]-4-yl)sulfonyl]ethyl]-1-naphthalenecarboxylate A solution of 4-chloro-4'-methylsulfone biphenyl (0.24 g, 0.88 mmol) in THF (25 mL) was treated with n-BuLi (0.35 mL, 0.88 mmoL) and stirred and -78° C. for 15 minutes to produce the lithiosulfone. A solution of methyl 2-(bromomethyl)-1-naphthoate (0.25 g, 0.88 mmoL) (preparation: *J. Org. Chem.* 1983, 48, 3869) in THF (5 mL) was added dropwise to the lithiosulfone and stirred at ambient temperature for 16 hours, poured into water, and extracted with ethyl acetate. The organic extracts were washed with brine, dried (MgSO$_4$), filtered, and concentrated. Purification on silica gel with 20% ethyl acetate/hexanes provided 0.12 g (29%) of the desired compound.

EXAMPLE 8B

2-[2-[(4'-chloro[1,1'-biphenyl]-4-yl)sulfonyl]ethyl]-1-naphthalenecarboxylic Acid To a solution of Example 8A (0.12 g, 0.26 mmoL) in MeOH (3 mL), H$_2$O (3 mL), and THF (15 mL) was added LiOH.H$_2$O (0.17 g, 3.84 mmoL). The mixture was stirred at 80° C. for 16 hours, poured into H$_2$O, and extracted with ethyl acetate. The combined organic extracts were washed with brine, dried (MgSO$_4$), filtered, and concentrated. Purification on silica gel with 2% MeOH/CH$_2$Cl$_2$ provided 0.02 g (20%) of the desired compound.

EXAMPLE 8C

2-[2-[(4'-chloro[1,1'-biphenyl]-4-yl)sulfonyl]ethyl]-N-hydroxy-1-naphthalenecarboxamide Example 8B was prepared according to the procedure described in Example 1F. mp 115° C.;

MS (ESI) m/e 464 (M−H)⁺, 466 (M+H)⁺, 488 (M+Na)⁺;
¹H NMR (d6-DMSO) δ 10.98 (s, 1H), 9.30 (s, 1H), 8.04–7.39 (m, 14H), 3.74–3.68 (m, 2H), 3.11–3.01 (m, 2H);
HRMS Calculated for $C_{25}H_{21}NO_4ClS$: 466.0880. Found: 466.0880.

EXAMPLE 9

N-hydroxy-2-[[[4'-trifluoromethoxy[1,1'-biphenyl]-4-yl)sulfonyl]amino]methyl]-1-naphthalenecarboxamide

EXAMPLE 9A

N-Boc-4-bromobenzenesulfonamide

A suspension of 4-bromophenylsulfonamide (3.5 g, 14.8 mmol) and di-tert-butyl dicarbonate (3.76 g, 17.0 mmol) in $CH_2Cl_2$ (100 mL) under nitrogen was treated with triethylamine (2.3 mL, 16.3 mmol) and DMAP (183 mg, 1.48 mmol) and stirred at room temperature for 12 hours. The reaction mixture was washed with IM HCl (2x25 mL), H2O (25 mL), and brine, dried ($Na_2SO_4$), filtered, and concentrated. Purification on silica gel with a gradient of 2% to 5% MeOH in $CH_2Cl_2$ afforded 4.46 g (90%) of the desired compound as white solid.

mp 127–128° C.;
MS (DCI) m/e 355/353 (M+NH₄)⁺;
¹H NMR (CDCl₃) δ 1.41 (s, 9H), 7.16 (br s, 1H), 7.69 (d, 2H), 7.89 (d, 2H).

EXAMPLE 9B

N-Boc-4'-(trifluoromethoxy)-[1,1'-biphenyl]-4-sulfonamide

A mixture of Example 9A (3.10 g, 9.22 mmol), 4-trifluoromethoxyphenylboronic acid (2.13 g, 10.14 mmol), absolute EtOH (15 mL), 2 M aqueous $Na_2CO_3$ (9.22 mL, 18.44 mmol), and toluene (65 mL) was sparged with $N_2$, treated with tetrakis(triphenylphosphine)paladium (0) (538 mg, 0.461 mmol), and heated at reflux for 1.25 hours. The reaction mixture was cooled, diluted with $H_2O$ (50 mL) and ethyl acetate (100 mL), and acidified to pH 3 with HOAc. The organic phase was washed with $H_2O$ and brine, dried ($Na_2SO_4$), filtered, and concentrated. Purification on silica gel with a gradient of $CH_2Cl_2$ to 2% MeOH/Cf₂CH₂ provided 3.40 g (88%) of the desired compound as a white solid.

MS (DCI) m/e 435 (M+NH₄)⁺;
¹H NMR (DMSO-d₆) δ 1.31 (s, 9H), 7.54 (d, J=8.8 Hz, 2H), 7.90 (d, J=8.8 Hz, 2H), 7.96 (s, 4H).

EXAMPLE 9C

1-Bromo-2-naphthalenemethanol

A solution of 1-bromo-2-naphthaldehyde (2.12 g, 8.91 mmol) in MeOH under $N_2$ at 0° C. was treated with $NaBH_4$ (0.51 g, 13.4 mmol), stirred for 15 minutes, quenched with acetone, and concentrated. Purification on silica gel with 5% ethyl acetate/$CH_2Cl_2$ provided 1.95 g (92%) of the desired compound as a white solid.

mp 101–102° C.;
MS (DCI) m/e 256/254 (M+NH₄)⁺;
¹H NMR (CDCl3) δ 2.09 (br d, 1H), 5.00 (s, 2H), 7.50–7.70 (m, 3H), 7.85 (d, J=8.8 Hz, 2H), 8.32 (d, J=8.9 Hz, 1H).

EXAMPLE 9D

N-Boc-N-[(1-bromo-2-naphthalenyl)methyl]-4'-(trifluoromethoxy)-[1,1'-biphenyl]-4-sulfonamide To a solution of Example 9C (3.37 g, 8.06 mmol) in THF (75 mL) under $N_2$ was added triphenylphosphine (5.34 g, 20.16 mmol), 1-bromo-2-naphthalenemethanol (1.59 g, 6.72 mmol), diethylazodicarboxylate (DEAD) (2.8 mL, 16.80 mmol), and the reaction was allowed to stir for 24 hours. The solvent was removed and the material was purified on silica gel with a gradient of 50% to 40% hexanes/$CH_2Cl_2$ to provide 3.81 g (89%) of the desired compound as a white foam.

MS (APCI) m/e 655/653 (M+NH₄)⁺;
¹H NMR (CDCl3) δ 1.32 (s, 9H), 5.38 (s, 2H), 7.31–7.87 (m, 1H), 8.00 (d, J=8.5 Hz, 2H), 8.32 (d, J=8.5 Hz, 1H).

EXAMPLE 9E 1,1-dimethylethyl 2-[[[[4'-(trifluoromethoxy)[1,1'-biphenyl]-4-yl]sulfonyl]amino]methyl]-1-naphthalenecarboxylate To a solution of Example 9D (1.50 g, 2.36 mmol) in THF (25 mL) under $N_2$ at −78° C. was added tert-butyllithium (1.7 M in pentane, 3.0 mL, 5.10 mmol). The resulting reddish-purple solution was stirred for 30 minutes at the same temperature and then quenched with HOAc (0.56 mL, 9.77 mmol) and warmed to RT. The solvent was removed and the resulting oil was dissolved in ethyl acetate (100 mL), washed with $H_2O$ and brine, dried (Na2SO₄), filtered, and concentrated. Purification on silica gel with a gradient of 10% hexanes/$CH_2Cl_2$ to 3% ethyl acetate/$CH_2Cl_2$ provided 1.13 g (86%) of the desired compound as a white foam.

MS (DCI) m/e 575 (M+NH₄)⁺;
¹H NMR (CDCl3) δ 1.57 (s, 9H), 4.26 (d, J=6.4 Hz, 2H), 5.32 (t, J=6.4 Hz, 1H), 7.29–7.96 (m, 14H);
HRMS (FAB) calculated 558.1562 for (M+H)⁺ for $C_{29}H_{27}F_3NO_5S$. Found 558.1543.

EXAMPLE 9F 1,1-dimethylethyl 2-[[[[4'-(trifluoromethoxy)[1,1'-biphenyl]-4-yl]sulfonyl](phenylmethoxycarbonyl)amino]methyl]-1-naphthalenecarboxylate A solution of Example 9E (1.255 g, 2.25 mmol) in DMF (20 mL) under $N_2$ at 0° C. was treated with NaH (60% dispersion in mineral oil, 180 mg, 4.50 mmol) and allowed to stirr for 30 minutes. Benzylchloroformate (0.68 mL, 4.50 mmol) was added, the mixture was allowed to stir for 2 hours, and HOAc was added. The solvent was removed and the residue was dissolved in ethyl acetate (100 mL), washed with $H_2O$ and brine, dried ($Na_2SO_4$), filtered, and concentrated. Purification over silica gel with 30% hexanes/$CH_2Cl_2$ provided 1.19 g (77%) of the desired compound as a white solid.

MS (ESI) m/e 709 (M+NH₄)⁺;
¹H NMR (CDCl3) δ 1.71 (s, 9H), 5.13 (s, 2H), 5.38 (s, 2H), 7.05–7.40 (m, 8H), 7.47–7.62 (m, 6H), 7.75–7.86 (m, 4H), 8.01 (d, 1H);
HRMS (FAB) calculated m/e=692.1930 for (m+H)⁺ for $C_{37}H_{33}F_3NO_7S$. Found m/e=692.1941.

EXAMPLE 9G

2-[[[[4'-(trifluoromethoxy)[1,1'-biphenyl]-4-yl]sulfonyl](phenylmethoxycarbonyl)amino]methyl]-1-naphthalenecarboxylic Acid A solution of Example 9F (1.19 g, 1.72 mmol) in $CH_2Cl_2$ (35 mL) under $N_2$ at −20° C. was treated with trifluoroacetic acid (13.3 mL, 0.172 mol) and allowed to stir at 0° C. 2 for 1 hour and then quenched with 2.6 M Na2CO3 (50 mL). The reaction mixture was reacidified to pH 3 with 1 M aq HCl, extracted with ethyl acetate. The combined ogranic layers were washed with brine, dried (Na$_2$SO$_4$), filtered, and concentrated (chasing with anhydrous toluene) to provide 1.096 g (100%) of the desired compound white powder.

MS (APCI) m/e 653 (M+NH$_4$)$^+$, 636 (M+H)$^+$;

$^1$H NMR (CDCl$_3$) δ 5.09 (s, 2H), 5.41 (s, 2H), 7.05–7.25 (m, 5H), 7.33 (d, J=8.8 Hz, 2H), 7.48 (d, J=8.5 Hz, 2H), 7.52–7.65 (m, 5H), 7.79 (d, J=8.8 Hz, 2H), 7.88 (m, 1H), 7.95 (d, J=8.5 Hz, 1H), 8.16 (d, 1H);

HRMS (FAB) calculated 636.1304 for (M+H)$^+$ for C$_{33}$H$_{25}$F$_3$NO$_7$S. Found 636.1318.

EXAMPLE 9H

N-hydroxy-2-[[[[4'-(trifluoromethoxy)[1,1'-biphenyl]-4-yl]sulfonyl](phenylmethoxycarbonyl)amino]methyl]-1-naphthalenecarboxamide To an ice cold solution of Example 9G (1.096 g, 1.72 mmol) in CH$_2$Cl$_2$ (12 mL) under N$_2$ was added DMF (5 drops) and oxalyl chloride (0.30 mL, 3.45 mmol), and the reaction was allowed to stir at room temperature for 1 hour. The solvent was then removed by rotary evaporation chasing with anhydrous toluene (5 mL), and the residue was taken up in CH$_2$Cl$_2$ (7 mL) and added to a 0° C. solution of hydroxylamine hydrochloride (1.21 g, 0.017 mol) and triethylamine (2.9 mL, 0.021 mol) in THF/H20 (2:1 v/v, 12 mL). After allowing the reaction mixture to stir at room temperature for 3 hours, ethyl acetate (100 mL) and H$_2$O (25 mL) were added, and the layers were separated, and the organic phase was washed with 1 M HCl (2×10 mL), saturated aqueous NaHCO$_3$ (10 mL), brine, dried (Na$_2$SO$_4$), filtered, and concentrated. The residue was triturated with CH$_2$Cl$_2$ (75 mL) and vacuum filtered to remove a solid impurity. The filtrate was concentrated and the residue purified on silica gel (1.9×6 cm) with a gradient of CH$_2$Cl$_2$ to 3% MeOH/CH$_2$Cl$_2$ +0.5% concentrated NH$_4$OH to obtain 0.459 g (410%) of the desired compound as light beige solid.

MS (ESI) m/e 668 (M+NH$_4$)$^+$, 651 (M+H)$^+$;

$^1$H NMR (CDCl$_3$) δ 5.05 (s, 2H), 5.22 (br s, 2H), 7.04 (d, J=7.3 Hz, 2H), 7.18 (t, J=7.3 Hz, 2H), 7.28--7.39 (m, 3H), 7.42 (d, J=7.7 Hz, 2H), 7.50–7.60 (m, 4H), 7.64 (d, J=8.4 Hz, 1H), 7.74 (d, J=8.1 Hz, 2H), 7.84–8.02 (m, 3H), 9.19 (br s, 1H);

HRMS (FAB) calculated 651.1413 for (M+H)$^+$ for C$_{33}$H$_{26}$F$_3$N$_2$O$_7$S. Found 651.1418.

EXAMPLE 9I

N-hydroxy-2-[[[4'-(trifluoromethoxy)[1,1'-biphenyl]-4-yl]sulfonyl]methyl]-1-naphthalenecarboxamide A mixture of Example 9H (0.456 g, 0.70 mmol) and 5% Pd—C (100 mg) in MeOH (10 mL) at 0° C. was hydrogenated under 1 atmosphere of hydrogen for 2 hours. The catalyst was removed by vacuum filtration through a 0.5 m polytetrafluoroethylene (PTFE) membrane and the filtrate was concentrated. Recrystallization from ethyl acetate/hexane provided 0.19 g (52%) of the desired compound as a white solid.

MS (ESI) m/e 539 (M+Na)$^+$, 534 (M+NH$_4$)$^+$, 517 (M+H)$^+$;

$^1$H NMR (CD$_3$OD) δ 4.29 (s, 2H), 7.39 (d, J=8.4 Hz, 2H), 7.47–7.60 (m, 3H), 7.70–7.79 (m, 4H), 7.81–7.90 (m, 3H), 7.95 (d, J=8.1 Hz, 2H);

Anal. calc'd for C$_{25}$H$_{19}$F$_3$N$_2$O$_5$S: C, 58.13; H, 3.71; N, 5.42. Found: C, 57.88; H, 3.75; N, 5.39.

EXAMPLE 10

N-hydroxy-2-[3-[(4'-methoxy[1,1'-biphenyl]-4-yl)sulfonyl]propyl]-1-naphthalenecarboxamide

EXAMPLE 10A 1-bromo-2-naphthalenepropanol

A solution of Example 3C (3.82 g, 14.5 mmol) in DMF and para-toluene- sulfonhydrazide (27 g, 145 mmol) was heated to reflux and treated with sodium acetate trihydrate (32.8 g, 241 mmol) in water (380 mL) over 3 hours. The mixture was allowed to stir at reflux for 2 hours, cooled, partitioned between CH$_2$Cl$_2$ and water. The organic layer was dried (Na$_2$SO$_4$), filtered, concentrated and purified on silica gel with a gradient of CH$_2$Cl$_2$ to 2% methanol/CH$_2$Cl$_2$ to provide 2.88 g (75%) of the desired compound as a pale yellow oil.

MS (DCI) mn/e 282, 284 (M+NH$_4$)$^+$.

EXAMPLE 10B

6-[3-(1-bromo-2-naphthalenyl)propoxy)-3,4-dihydro-2H-pyran

A mixture of Example 10A (2.96 g, 11.2 mmol) and 3,4-dihydro-2H-pyran (2.04 mL, 22.4 mmol) in CH$_2$Cl$_2$ and was stirred at 0° C. for 10 minutes and at room temperature for 40 minutes. The reaction mixture was partitioned between CH$_2$Cl$_2$ and water, the organic layer dried (Na$_2$SO$_4$), filtered, concentrated, and purified on silica gel with 10% ethyl acetate/hexanes to provide 3.73 g (95%) of the desired compound as an yellow oil.

MS (DCI) m/e 366, 368 (M+NH$_4$)$^+$.

EXAMPLE 10C

2-[3-(3,4-dihydro-2H-pyran-6-yloxy)propyl]-1-naphthalenecarboxylic Acid

Example 10B was prepared according to the procedure described in Example 1E.

MS (DCI) m/e 313 (M-H)-, 337 (M+Na)$^+$, 332 (M+NH$_4$)$^+$.

EXAMPLE 10D

Phenylmethyl 2-[3-(3,4-dihydro-2H-pyran-6-yloxy)propyl]-1-naphthalenecarboxylate A solution of Example 10C (2.05 g, 6.53 mmol) in DMF (25 mL) was treated with cesium carbonate (3.2 g, 9.8 mmol) and benzylbromide (1.16 mL, 9.75 mmol), stirred at 60° C. for 40 minutes, partitioned between ethyl acetate and water, dried (Na$_2$SO$_4$), filtered, concentrated and purified on silica gel with 7% ethyl acetate/hexanes to provide 2.0 g (76%) of the desired compound as an yellow oil.

MS (DCI) m/e 422 (M+NH$_4$)$^+$.

EXAMPLE 10E

Phenylmethyl 2-(3-hydroxypropyl)-1-naphthalenecarboxylate

A solution of Example 10D (2.0 g, 4.95 mmol) in methanol was treated with para-toluenesulfonic acid hydrate (84 mg, 0.44 mmol), stirred at room temperature for 2 hours, partitioned between ethyl acetate and water, dried (Na$_2$SO$_4$), filtered, concentrated and purified on silica gel with 30% ethyl acetate/hexanes to provide 1.5 g (95%) of the desired compound as an yellow oil.

MS (DCI) m/e 321 (M+H)$^+$, 338 (M+NH$_4$)$^+$.

EXAMPLE 10F

Phenylmethyl 2-[3-[(4-bromophenyl)thio]propyl]-1-naphthalenecarboxylate

The desired compound was prepared by coupling Example 10E and 4-bromothiophenol using the standard Mitsunubu conditions described in Example 7A.

MS (DCI) mle 508, 510 (M+NH$_4$)$^+$.

EXAMPLE 10G

Phenylmethyl 2-[3-[(4'-methoxy[1,1'-biphenyl]-4-yl)thio]propyl]-1-naphthalenecarboxylate The desired compound was prepared by reacting Example 1F and 4-methoxybenzene boronic acid under the Suzuki coupling conditions described in Example 6C.

MS (DCI) m/e 536 (M+NH$_4$)$^+$.

EXAMPLE 10H

N-hydroxy-2-[3-[(4'-methoxy[1,1'-biphenvyl]-4-yl)sulfonyl]propyl]-1-naphthalenecarboxamide Example 10G was prepared according to the procedure described in examples 6E, 6F, and 6G.

m.p. 105.4° C. decomposed;

MS (APCI) m/e 585 (M+Cl)−, 568 (M+NH$_4$)$^+$;

$^1$H NMR (300 MHz, DMSO-d$_6$) δ 1.90–2.02 (m, 2H), 2.757–2.806 (t, 2H, J=6.9 Hz), 3.819 (s, 3H), 7.058 (td, 2H, J=2.1, 8.7 Hz), 7.372–7.400 (d, 1H, J=8.4 Hz), 7.470–7.572 (2H), 7.704–7.758 (m, 3H), 7.880–7.908 (m, 6H), 9.226 (s, 1H), 10.968 (s, 1H);

Anal. calc'd for C$_{27}$H$_{25}$NO$_5$S.0.5 H$_2$O, C, 66.92; H, 5.40; N, 2.89. Found: C, 66.93; H, 5.37; N, 2.67.

EXAMPLE 11

N-hydroxy-2-[4-(4'-methoxy[1,1'-biphenyl]-4-yl)-4-oxobutyl]-1-naphthalenecarboxamide

EXAMPLE 11A 2-propenyl 2-[3-(3,4-dihydro-2H-pyran-6-yloxy)propyl]-1-naphthalenecarboxylate The desired compound was prepared according to the procedure described in Example 10D, except substituting allylbromide for benzylbromide in Example 1 OD.

MS (APCI) m/e 355 (M+H)$^+$, 372 (M+NH$_4$)$^+$.

EXAMPLE 11B 2-propenyl 2-(3-hydroxypropyl)-1-naphthalenecarboxylate

The desired compound was prepared according to the procedure described in Example 10E, except substituting 11A for 10D in Example 10E.

MS (ESI) m/e 271 (M+H)$^+$, 288 (M+NH$_4$)$^+$.

EXAMPLE 11C

1-[(2-propenyloxy)carbonyl]-2-naphthalenepropanoic acid

A solution of Example 11B (1.4 g, 5.18 mmol) in acetone (20 mL) was treated with Jones reagent (CrO$_3$/H$_2$SO$_4$) until the orange color persisted, quenched with isopropyl alcohol, partitioned between ethyl acetate and water. The organic layer was washed with water, dried (Na$_2$SO$_4$), filtered, concentrated, and purified on silica gel with a gradient of 30% ethyl acetate/hexanes to 10% MeOH/dichloromethane to provide 1.27 g (86%) of the desired compound as an yellow oil.

MS (ESI) m/e 283 (M-H)−.

EXAMPLE 11D

Methyl 1-[(2-propenyloxy)carbonyl]-2-naphthalenbutanoate

A solution of Example 11C (600 mg, 2.11 mmol) in benzene (5 mL) was treated with thionyl chloride (0.184 mL, 2.53 mmol) at room temperature and allowed to stir for 1 hour. The reaction mixture was concentrated to dryness, redissolved in benzene (5 mL), treated with CH$_2$N$_2$/Et$_2$O at 0° C., and allowed to stir at room temperature for 2 hours. The reaction mixture was concentrated under a stream of nitrogen, and the residue was dissolved in methanol (30 mL), treated with silver benzoate (1.1 g, 4.85 mmol) and triethylamine (11 mL, 79.7 mmol) and allowed to stir at room temperature for 1.5 hours. The organic layer was partitioned between saturated sodium bicarbonate and ethyl acetate, dried (Na$_2$SO$_4$), filtered, concentrated and purified on silica gel with 10% ethyl acetate/hexanes to provide 402 mg (61%) of the desired compound as an yellow oil.

MS (DCI) m/e 330 (M+NH$_4$)$^+$.

EXAMPLE 11E

1-[(2-propenyloxy)carbonyl]-2-naphthalenbutanoic Acid

A solution of Example 11D (400 mg, 1.28 mmol) in isopropyl alcohol (5 mL) was treated with lithium hydroxide (1.0M, 1.28 mL, 1.28 mmol), stirred at room temperature for 1.5 hours, and partitioned between ethyl acetate and water. The aqueous layer was then acidified with 1N HCl, extracted with dichloromethane, dried (Na$_2$SO$_4$), filtered, and concentrated to provide 282.8 mg (74%) of the desired compound as a yellow oil.

MS (ESI) m/e 299 (M+H)$^+$, 297 (M-H)−, 321 (M+Na)$^+$.

EXAMPLE 11F 2-propenyl 2-[4-(4'-methoxy[1,1'-biphenyl]-4-yl)-4-oxobutly]-1-naphthalenecarboxylate A solution of Example 11E (282 mg, 0.946 mmol) in benzene (5 mL) was treated with thionyl chloride (0.138 mL, 1.89 mmol) and DMF (1 drop), stirred at room temperature for 30 minutes, concentrated to dryness and redissolved in dichloromethane (5 mL). The resulting solution was treated with 4-methoxybiphenyl (348 mg, 1.89 mmol) and aluminum chloride (377 mg, 2.84 mmol) at 0° C., stirred at room temperature for 40 minutes, quenched with ice-water, extracted with dichloromethane, dried (Na$_2$SO$_4$), filtered, concentrated and purified on silica gel with a gradient of 5% to 20% ethyl acetate/hexanes to provide 200 mg (45%) of the desired compound contaminated with 30% of the ortho substituted isomer.

MS (APCI) m/e 465 (M+H)$^+$, 482 (M+NH$_4$)$^+$.

EXAMPLE 11G

2-[4-(4'-methoxy[1,1'-biphenyl]-4-yl)-4-oxobutyl]-1-naphthalenecarboxylic Acid

A solution of Example 11F (200 mg, 0.431 mmol) in dichloromethane (5 mL) at room temperature was treated with tetrakis(triphenylphosphine)palladium (43 mg, 0.0375 mmol), triphenylphosphine (19.6 mg, 0.075 mmol), piperidine (0.0447 mL, 0.452 mmol), and allowed to stir at room temperature for 30 minutes. The reaction mixture was diluted with 0.5 N HCl, and extracted with dichloromethane. The organic layer was dried ($Na_2SO_4$), filtered, concentrated, and purified on silica gel with 10% methanol/ $CH_2Cl_2$ to provide 197 mg (100%) of the desired compound as an white solid.

MS (ESI) m/e 425 $(M+H)^+$, 423 (M-H)–, 447 $(M+Na)^+$.

EXAMPLE 11H

N-hydroxy-2-[4-(4'-methoxy[1,1'-biphenyl]-4-yl)-4-oxobutyl]-1-naphthalenecarboxamide Example 11G was prepared according to the procedure described in Example 1F.

m.p. 160–163° C. decomposed;

MS (APCI) m/e 440 $(M+H)^+$, 457 $(M+NH_4)^+$;

$^1$H NMR (300 MHz, DMSO-$d_6$) δ 2.008–2.037 (m, 2H), 2.799–2.830 (t, 2H, J=4.5 Hz), 3.072–3.101 (t, 2H, J=4.2 Hz), 3.813 (s, 3H), 7.049–7.066 (d, 2H, J=5.1 Hz), 7.476–7.551 (3H), 7.694–7.711 (d, 2H, J=5.1 Hz), 7.758–7.784 (3H), 7.906–7.935 (t, 2H, J=3.9 Hz), 7.997–8.014 (d, 2H, J=5.1 Hz), 9.223 (s, 1H), 10.974 (s, 1H);

HRMS (FAB) calculated m/e for $(M+H)^+$:$C_{28}H_{26}NO_4$, 440.1862. Found 440.1882.

EXAMPLE 12

N-hydroxy-2-[4-(4'-methoxy[1,1'-biphenyl]-4-yl)-3-oxopropyl]-1-naphthalenecarboxamide

EXAMPLE 12A 2-propenyl 2-[3-(4'-methoxy[1,1'-biphenyl]-4-yl)-3-oxopropyl]-1-naphthalenecarboxylate The desired compound was prepared according to the procedure described in Example 11F, except substituting Example 11C for Example 11E.

MS (APCI) m/e 451 $(M+H)^+$.

EXAMPLE 12B

N-hydroxy-2-[3-(4'-methoxy[1,1'-biphenyl]-4-yl)-3-oxopropyl]-1-naphthalenecarboxamide Example 12A was prepared according to the procedures described in examples 11G and 11H.

MS (APCI) m/e 426 $(M+H)^+$, 448 $(M+Na)^+$;

$^1$H NMR (300 MHz, DMSO-$d_6$) δ 3.00–3.11 (t, 2H, J=9 Hz), 3.40–3.50 (m, 2H), 3.81 (s, 0.8H), 3.89 (s, 0.2H), 7.02–7.09 (d, 2H, J=9 Hz), 7.23–7.97 (1H), 8.79–8.06 (d, 2H, J=3 Hz), 9.31 (s, 1H), 11.05 (s, 1H);

Anal. calc'd for $C_{27}H_{23}NO_4$·0.75 MeOH, C, 74.14; H, 5.83; N, 3.11. Found: C, 74.08; H, 5.83; N, 2.73.

EXAMPLE 13

N-hydroxy-2-[2-[[3'-cyamomethyl)[1,1'-biphenyl]-4-yl]sulfonyl]ethoxy]-1-naphthalenecarboxamide Example 7A, was prepared according to the procedure described in examples 7B and 7C, except substituting 3-cyanomethylphenyl boronic acid in place of 4-methoxyboronic acid in Example 7B.

MS (ESI+) m/e 487 $(M+H)^+$;

$^1$H NMR (300 MHz, DMSO-d,) δ 3.90 (d, J=6 Hz, 2H), 4.13 (s, 2H), 4.47 (d,J=6 Hz, 2H), 7.38–7.60 (m, 5H), 7.68–7.75 (m, 3H), 7.88 (d, J=8 Hz, 1H), 7.92–7.98 (m, 3H), 8.06 (d, J=8 Hz, 1H), 9.20 (d, J=15 Hz, 1H).

EXAMPLE 14

2-[2-[(4'-cyano[1,1'-biphenyl]-4-yl)oxy]ethoxy]-N-hydroxy-1-naphthalenecarboxamide

EXAMPLE 14A

4'-(2-hydroxyethoxy)[1,1'-biphenyl]-4-carbonitrile

To a solution of 4'-hydroxy-4-biphenylcarbonitrile (1.014 g, 5.19 mmol) in 10 mL DMF was added potassium carbonate (2.15 g, 15.6 mmol, 3 eq.) and 2-bromoethylacetate. After two hours at 50° C., the reaction mixture was cooled to room temperature, diluted with 50 mL EtOAc, washed with $H_2O$ (3×10 mL), dried ($Na_2SO_4$), filtered, and concentrated to provide a white solid. The solid was dissolved in 20 mL MeOH and 5 mL $H_2O$ and potassium carbonate (2.15 g, 15.6 mmol) were added. After 30 minutes, the MeOH was evaporated and the crude reaction was taken up in EtOAc and washed with $H_2O$ (10 mL×3), dried ($Na_2SO_4$), filtered, concentrated, and purified on silica gel to provide 0.967g (78%) of the desired compound.

1H NMR (300 MHz, $CDCl_3$) δ 7.79–7.60 (m, 4H), 7.57–7.52 (m, 2H), 7.05–7.01 (m, 2H), 4.15 (2H), 4.08–3.98 (m, 2H), 2.04 (t, 1H).

EXAMPLE 14B

4'-(2-hydroxyethoxy)[1,1'-biphenyl]-4-carbonitrile Methanesulfonate

To a solution of example 14A (150 mg, 0.63 mmol) in 6 mL $CH_2Cl_2$ at 0° C. was added triethylamine (127 mg, 1.26 mmol, 2 eq.) followed by methanesulfonyl chloride (108 mg, 0.94 mmol, 1.5 eq.). After stirring at ambient temperature for 4 h, the reaction mixture was concentrated and purified on silica gel with 25% EtOAc/hexanes to provide 185 mg (92%) of the desired compound as a white solid.

1H NMR ($CDCl_3$, 300 MHz) δ 7.73–7.70 (m, 2H), 7.66–7.62 (m, 211), 7.58–7.52 (m, 211), 7.04–6.99 (m, 211), 4.63–4.60 (m, 2H), 4.33–4.30 (m, 2H), 3.11 (s, 3H).

EXAMPLE 14C

Phenylmethyl 2-[2-[(4'-cyano[1,1'-biphenyl]-4-yl)oxy]ethoxy]-1-naphthalenecarboxylate To a solution of example 6A (147 mg, 0.53 mmol) and example 14B (168 mg, 0.53 mmol) in 6 mL DMF was added $K_2CO_3$ (219 mg, 1.59 mmol). The reaction was allowed to stir at 50° C. for 14 hours and was diluted with EtOAc, washed with $H_2O$ (3×10 mL), dried ($Na_2SO_4$), filtered, concentrated, and purified on silica gel with 25% ethyl acetate/hexanes to give 225 mg (85%) of the desired compound as a white solid.

$^1$H NMR (300 MHz, $CDCl_3$) δ 7.91 (d, 1H), 7.82–7.63 (m, 6H), 7.55–7.28 (m, 10H), 7.02–6.97 (m, 2H), 5.45 (s, 2H), 4.49 (dd, 2H), 4.26 (dd, 2H).

EXAMPLE 14D

2-[2-[(4'-cyano[1,1'-biphenyl]-4-yl)oxy]ethoxy]-N-hydroxy-1-naphthalenecarboxamide Example 14C was converted to the title compound following the procedures of examples 6F and 1F.

1H NMR (300 MHz, DMSO-$d_6$) δ 9.18 (d, J=1.7 Hz, 1H), 7.96 (d, J=9.2 Hz, 1H), 7.87–7.83 (m, 5H), 7.75–7.70 (m,

3H), 7.55–7.49 (m, 3H), 4.43–7.38 (m, 1H), 7.16–7.13 (m, 2H), 4.54–4.51 (m, 2H), 7.40–7.38 (m, 2H);
MS (APCI) m/e 425(M+H)+.

EXAMPLE 15

N-hydroxy-2-[2-[[(4'-methoxy[1,1'-biphenyl]-4-yl) sulfonyl]axino]ethyl]-1-naphthalenecarboxamide The title compound was prepared following the procedures of example 9, except substituting 4-methoxyphenyl boronic acid for 4-trifluomethoxyphenyl boronic acid in example 9B and 1-bromo 2-(2'-hydroxyethyl) napthalene for 1-bromo-2napthalenemethanol in example 9C.

1H NMR (300 MHz, CD$_3$OD) δ 7.84 (d, 1H), 7.74–7.69 (m, 4H), 7.56–7.51 (m, 5H), 7.48–7.43 (m, 1H), 7.26 (d, 1H), 7.02 (d, 2H), 3.85 (s, 3H), 3.27–3.25 (m, 2H), 2.92 (t, 2H);
HRMS (FAB) C$_{26}$H$_{24}$N$_2$O$_5$S MH+ Calcd. 477.1484, found 477.1479.

EXAMPLE 16

N-hydroxy-2-[2-(4-phenoxyphenoxy)ethyl]-1-naphthalenecarboxamnide

The title compound was prepared following the procedures of example 1, except substituting 4-(4'-phenoxy)-phenol for 4-chloro-4'-biphenyl in example 1D.

1H NMR (300 MHz, DMSO-$d_6$) δ 9.32 (bs, 1H), 7.96–7.90 (m, 2H), 7.81–7.77 (m, 1H), 7.59–7.50 (m, 3H), 7.36–7.31 (m, 2H), 7.08–7.04 (m, 1H), 6.97 (s, 5H), 6.93–6.89 (m, 2H), 4.23 (t, 2H), 3.18 (t, 2H);
MS (CI) 400 (MH)+.

What is claimed is:
1. A compound of formula I:

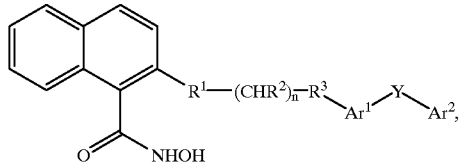

I or a pharmaceutically acceptable salt or produrug thereof, wherein
R$^1$ is selected from the group consisting of (a) a covalent bond, (b) —O—, and (c) —S(O)$_q$— wherein q is 0, 1, or 2;
R$^2$ is hydrogen or alkyl;
R$^3$ is selected from the group consisting of (a) —HNSO$_2$—, (b) —O—, (c) —S(O)$_q$—, (d) —C(=O)—, and (e) —C(=NOH)—; and
n is 1, 2, or 3;
Ar$^1$ is phenyl substituted with 0, 1, or 2 substituents independently selected from the group consisting of (a) alkyl, (b) perfluoroalkyl, (c) halo, (d) haloalkyl, (e) alkoxy, (f) hydroxy, (g) hydroxyalkyl, (h) alkoxyalkyl, and (i) nitro;
Y is selected from the group consisting of (a) a covalent bond, (b) —O—, (c) alkylene, (d) piperidineneyl, (e) alkenylene, (f) alkynylene, (g) —S(O)$_q$—, (h) —NHC(=O)—, and (i) —C(=O)—; and
Ar$^2$ is selected from the group consisting of (a) phenyl, (b) pyridyl, (c) pyrazinyl, (d) pyridazinyl, (e) furyl, (f) thienyl, (g) isoxazolyl, (h) oxazolyl, (i) thiazolyl, and (j) isothiazolyl wherein the groups defining Ar$^2$ are substituted with 0, 1, 2, or 3 substituents independently selected from the group consisting of (1) alkyl, (2) alkoxy, (3) alkoxyalkoxy, (4) alkyloxycarbonylalkyl, (5) alkoxyalkyl, (6) cyano, (7) cyanoalkyl, (8) halo, (9) haloalkyl, (10) hydroxy, (11) hydroxyalkyl, (12) thioalkoxy, (13) thioalkoxyalkyl, (14) phenylalkoxy, (15) phenoxy, (16) —N(R$^2$)SO$_2$R$^{2'}$ wherein R$^2$ is defined previously and R$^{2'}$ is hydrogen or alkyl, (17) —SO$_2$N(R$^2$)(R$^{2'}$) wherein R$^2$ and R$^{2'}$ are defined previously, (18) phenoxyalkyl, (19) (heterocycle)oxy, (20) (heterocycle)oxyalkyl, (21) perfluoroalkyl, (22) perfluoroalkoxy, (23) sulfinylalkyl, (24) sulfonylalkyl, (25)

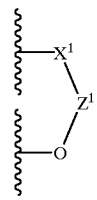

wherein X$^1$ is selected from the group consisting of —CH$_2$—, —CH$_2$O—, and —O—, and Z$^1$ is —C(=O)— or —(C(R$^2$)$_2$)$_v$—, wherein R$^2$ is defined previously, and v is 1–3, and (26) -alkyl-NR$^x$R$^y$ wherein R$^x$ and R$^y$ are independently selected from the group consisting of
(i) alkyl,
(ii) phenyl substituted with 0, 1, or 2 substituents selected from the group consisting of halo and alkoxy, and
(iii) phenylalkyl wherein the phenyl group is substituted with 0, 1, or 2 substituents selected from the group consisting of halo and alkoxy.
2. A compound according to claim 1 wherein R$^1$ is a covalent bond and R$^3$ is —O—.
3. A compound according to claim 2 selected from the group consisting of
2-[2-[(4'-chloro[1,1'-biphenyl]-4-yl)oxy]ethyl]-N-hydroxy-1-naphthalenecarboxamide,
2-[2-[(4'-chloro[1,1'-biphenyl]-3-yl)oxy]ethyl]-N-hydroxy-1-naphthalenecarboxamide,
2-[3-[(4'-chloro[1,1 '-biphenyl]-4-yl)oxy]propyl]-N-hydroxy-1-naphthalenecarboxamide,
and N-hydroxy-2-[2-(4-phenoxyphenoxy)ethyl]-1-naphthalenecarboxamide.
4. A compound according to claim 1 wherein R$^1$ is —O— or a covalent bond and R$^3$ is C(=O)— or —C(=NOH)—.
5. A compound according to claim 4 selected from the group consisting of
2-[2-(4'-chloro[1,1'-biphenyl]-4-yl)-2-oxoethoxy]-N-hydroxy-1-naphthalenecarboxamide,
2-[2-(4 '-chloro[ 1,1 '-biphenyl]-4-yl)-2-(hydroxyimino) ethoxy]-N-hydroxy-1-naphthalenecarboxamide,
N-hydroxy-2-[4-(4'-methoxy[1,1'-biphenyl]-4-yl)-4-oxobutyl]-1-naphthalenecarboxamide, and
N-hydroxy-2-[4-(4'-methoxy[1,1'-biphenyl]-4-yl)-3-oxopropyl]-1-naphthalenecarboxamide.
6. A compound according to claim 1 wherein R$^1$ is —O— and R$^3$ is —S(O)$_q$— wherein q is defined previously.
7. A compound according to claim 6 selected from the group consisting of 2-[[2-(4'-chloro[1,1'-biphenyl]-4-yl)sulfonyl]ethoxy]-N-hydroxy-1-naphthalenecarboxamide, N-hydroxy-2-[2-[(4'-methoxy[1,1'-biphenyl]-4-yl)sulfonyl]ethoxy]-1-naphthalenecarboxamide, and N-hydroxy-2-[2-[[3'-(cyanomethyl)[1,1'-biphenyl]-4-yl]sulfonyl]ethoxy]-1-naphthalenecarboxamide.

8. A compound according to claim 1 wherein $R^1$ is a covalent bond and $R^3$ is —S(O)$_q$— wherein q is defined previously.

9. A compound according to claim 8 selected from the group consisting of

2-[2-[(4'-chloro[1,1'-biphenyl]-4-yl)sulfonyl]ethyl]-N-hydroxy-1-naphthalenecarboxamide and N-hydroxy-2-[3-[(4'-methoxy[1,1'-biphenyl]-4-yl)sulfonyl]propyl]-1-naphthalenecarboxamide.

10. A compound according to claim 1 wherein $R^1$ is a covalent bond and $R^3$ is —NHSO$_2$—.

11. A compound according to claim 10 which is

N-hydroxy-2-[[[(4'-trifluoromethoxy[1,1'-biphenyl]-4-yl)sulfonyl]amino]methyl]-1-naphthalenecarboxamide and N-hydroxy-2-[2-[[(4'-methoxy[1,1'-biphenyl]-4-yl)sulfonyl]amino]ethyl]-1-naphthalenecarboxamide.

12. A compound according to claim 1 wherein $R^1$ and $R^3$ are —O—.

13. A compound according to claim 12 which is

2-[2-[(4'-cyano[1,1'-biphenyl]-4-yl)oxy]ethoxy]-N-hydroxy-1-naphthalenecarboxamide.

14. A composition for inhibiting matrix metalloproteinases comprising a pharmaceutical carrier and a therapeutically effective amount of a compound of claim 1.

* * * * *